United States Patent
Fujiwara et al.

(10) Patent No.: US 7,927,290 B2
(45) Date of Patent: Apr. 19, 2011

(54) BLOOD TEST APPARATUS

(75) Inventors: Masaki Fujiwara, Ehime (JP);
Toshihiro Akiyama, Ehime (JP);
Yoshinori Amano, Ehime (JP)

(73) Assignee: PANASONIC Corporation, Osaka (JP)

( * ) Notice: Subject to any disclaimer, the term of this patent is extended or adjusted under 35 U.S.C. 154(b) by 190 days.

(21) Appl. No.: 12/159,904

(22) PCT Filed: Dec. 28, 2006

(86) PCT No.: PCT/JP2006/326262
§ 371 (c)(1),
(2), (4) Date: Jul. 2, 2008

(87) PCT Pub. No.: WO2007/077930
PCT Pub. Date: Jul. 12, 2007

(65) Prior Publication Data
US 2009/0281455 A1    Nov. 12, 2009

(30) Foreign Application Priority Data

| Jan. 5, 2006 | (JP) | 2006-000354 |
| Jan. 5, 2006 | (JP) | 2006-000355 |
| Jan. 5, 2006 | (JP) | 2006-000356 |
| Jan. 5, 2006 | (JP) | 2006-000357 |
| Jan. 5, 2006 | (JP) | 2006-000358 |
| Jan. 31, 2006 | (JP) | 2006-022040 |

(51) Int. Cl.
*A61B 5/00* (2006.01)
*A61B 17/14* (2006.01)
*A61B 17/32* (2006.01)
*B65D 81/00* (2006.01)

(52) U.S. Cl. ........ 600/576; 600/573; 600/575; 600/577; 600/578; 600/579; 600/583; 606/181

(58) Field of Classification Search ............ 600/573, 600/575, 576, 577, 578, 579, 583; 606/181
See application file for complete search history.

(56) References Cited

U.S. PATENT DOCUMENTS
6,027,459 A    2/2000    Shain et al.
(Continued)

FOREIGN PATENT DOCUMENTS
EP    1112717    7/2001
(Continued)

OTHER PUBLICATIONS
U.S. Appl. No. 12/162,612 to Fujiwara et al., which was filed Jul. 30, 2008.
(Continued)

*Primary Examiner* — Max Hindenburg
*Assistant Examiner* — Devin Henson
(74) *Attorney, Agent, or Firm* — Greenblum & Bernstein, P.L.C.

(57) ABSTRACT

A blood test apparatus wherein a blood collection needle and a blood sensor can be easily attached and detached so that a burden or pain of a patient can be relieved. More specifically speaking, a blood test apparatus wherein a holder, a lancet, a blood collection needle and a blood sensor are united together as a blood sampling cartridge that is detachably mounted to the apparatus body. When this blood sampling cartridge is attached, a plunger involved in the apparatus body holds the lancet and connectors involved in the apparatus body come into contact with the blood sensor. It is preferable that the contact points with the blood sensor of the individual connectors are located at intervals at the same angle centering on a definite point.

37 Claims, 26 Drawing Sheets

U.S. PATENT DOCUMENTS

| | | | |
|---|---|---|---|
| 6,063,039 | A | 5/2000 | Cunningham et al. |
| 6,071,249 | A | 6/2000 | Cunningham et al. |
| 6,071,251 | A | 6/2000 | Cunningham et al. |
| 6,093,156 | A | 7/2000 | Cunningham et al. |
| 6,206,841 | B1 | 3/2001 | Cunningham et al. |
| 6,283,926 | B1 | 9/2001 | Cunningham et al. |
| 6,306,104 | B1 | 10/2001 | Cunningham et al. |
| 6,706,159 | B2 | 3/2004 | Moerman et al. |
| 6,837,858 | B2 | 1/2005 | Cunningham et al. |
| 7,378,007 | B2 | 5/2008 | Moerman et al. |
| 2001/0031931 | A1 | 10/2001 | Cunningham et al. |
| 2002/0169393 | A1 | 11/2002 | Cunningham et al. |
| 2003/0144608 | A1 | 7/2003 | Kojima et al. |
| 2004/0209350 | A1 | 10/2004 | Sakata |
| 2005/0123443 | A1 | 6/2005 | Fujiwara et al. |
| 2005/0288698 | A1 | 12/2005 | Matsumoto |
| 2006/0047220 | A1 | 3/2006 | Sakata et al. |
| 2006/0091006 | A1 * | 5/2006 | Wang et al. ............... 204/403.02 |
| 2006/0116607 | A1 | 6/2006 | Nakamura et al. |
| 2006/0161077 | A1 | 7/2006 | Takinami |
| 2006/0271084 | A1 | 11/2006 | Schraga |
| 2007/0078360 | A1 | 4/2007 | Matsumoto et al. |
| 2009/0069717 | A1 | 3/2009 | Kojima et al. |
| 2009/0069718 | A1 | 3/2009 | Kojima et al. |
| 2009/0069719 | A1 | 3/2009 | Kojima et al. |
| 2009/0093694 | A1 | 4/2009 | Kojima et al. |
| 2009/0093736 | A1 | 4/2009 | Kojima et al. |
| 2009/0105615 | A1 | 4/2009 | Kojima et al. |

FOREIGN PATENT DOCUMENTS

| | | | |
|---|---|---|---|
| EP | 1285629 | | 2/2003 |
| EP | 1541087 | | 6/2005 |
| EP | 1541088 | | 6/2005 |
| EP | 1683483 | | 7/2006 |
| JP | 2000-000231 | A | 1/2000 |
| JP | 2000-116628 | A | 4/2000 |
| JP | 2000-232973 | A | 8/2000 |
| JP | 2001-515377 | A | 9/2001 |
| JP | 2003-524496 | A | 8/2003 |
| JP | 2004-033376 | A | 2/2004 |
| JP | 2004-057490 | A | 2/2004 |
| JP | 2005-110712 | A | 4/2005 |
| WO | 01/64105 | A1 | 9/2001 |
| WO | 03/013356 | A1 | 2/2003 |
| WO | 2004/112613 | A1 | 12/2004 |
| WO | 2005/039413 | | 5/2005 |
| WO | 2006/130482 | | 12/2006 |
| WO | WO 2007045411 | A1 * | 4/2007 |

OTHER PUBLICATIONS

U.S. Appl. No. 12/162,627 to Amano et al., which was filed Jul. 30, 2008.

U.S. Appl. No. 12/278,825 to Amano et al., which was filed Aug. 8, 2008.

Abstract of WO 0164105, Aug. 19, 2003.

* cited by examiner

BLOOD TEST APPARATUS

TECHNICAL FIELD

The present invention relates to a blood test apparatus. More particularly, the present invention relates to an apparatus measuring the blood sugar level in blood.

BACKGROUND ART

Diabetes patients need to measure the blood sugar level (glucose level) regularly, and inject insulin based on the blood sugar level to maintain a normal blood sugar level. To maintain the normal blood sugar level, diabetes patients need to measure the blood sugar level frequently, sample a small amount of blood from fingertips of the patients using a blood test apparatus, and measure the blood sugar level of the sampled blood.

FIG. 28 shows an example of the conventional blood test apparatus (see Patent Document 1). Blood test apparatus 1 has cylindrically-shaped housing 2, plunger 3 that moves back and forth inside housing 2, lancet 4 that has one end 4a held by plunger 3 and the other end 4b attached with blood collection needle 5, and blood sensor (hereinafter "sensor") 6 attached to one end 2a of housing 2.

Sensor 6 of blood test apparatus 1 is made to abut on skin 7 of the patient. Latch between convex part 9a of handle 9 connected to plunger 3 and concave part 2b formed on housing 2 is disengaged. Plunger 3 urged by spring 10 is thereby propelled in the direction of arrow 8. Lancet 4 held by plunger 3 and blood collection needle 5 attached to the lancet 4 are also propelled in the direction of arrow 8.

Blood collection needle 5 that is propelled forward goes through sensor 6 and makes a tiny prick on skin 7. The blood flowing out from the prick is detected by a detecting section of sensor 6, converted to an electric signal, and led to connection electrode 6a. Connection electrode 6a is connected with measuring circuit 12 via connector 11. Measuring circuit 12 calculates the blood sugar level of the sampled blood and the calculation result is displayed on display section 13.

Further, a body fluid measuring apparatus that has an apparatus body and an attachment with a sensor and a blood collection needle, is reported (see Patent Document 2).
Patent Document 1: Japanese Patent Application Publication No. 2003-524496
Patent Document 2: Japanese Patent Application Laid-Open No. 2000-000231

DISCLOSURE OF INVENTION

Problems to be Solved by the Invention

However, above-described blood test apparatus 1 needs to attach lancet 4 to which blood collection needle 5 is attached, to plunger 3 as preparation before use and attach sensor 6 to one end 2a of housing 2, and this work is troublesome.

This preparatory work will be further described. First, used sensor 6 attached to blood test apparatus 1 is removed. Next, plunger 3 is moved forward to one end 2a of housing 2. Lancet 4, to which new blood collection needle 5 is attached, is then attached to plunger 3. Next, plunger 3 is moved backward, and blood collection needle 5 is pulled inside housing 2. In a state where blood collection needle 5 is pulled inside housing 2, new sensor 6 is attached to one end 2a of housing 2. In this way, preparation is not completed until such many manipulation steps are performed.

Further, the body fluid measuring apparatus that has an apparatus body and an attachment with a sensor and a blood collection needle, disclosed in Patent Document 2, is not discussed sufficiently towards practical use. For example, device for attaching an attachment to an apparatus body; device for puncturing the skin with a puncturing body (blood collection needle) stably; and mechanism for leading sampled blood to the sensor efficiently, are not discussed. Therefore, the body fluid measuring apparatus is not practical.

The present invention provides a blood test apparatus that makes it possible to attach and remove a blood collection needle and a blood sensor in a simple manner, and an apparatus that alleviates the load and pain of the patient.

Means for Solving the Problem

In the blood test apparatus of the present invention, a holder, lancet, blood collection needle and blood sensor are integrated as a blood sampling cartridge which can be inserted to and removed from the apparatus detachably, and, when the blood sampling cartridge is attached, a plunger included in the apparatus holds the lancet, and connectors included in the apparatus are arranged so as to contact with the blood sensor.

Advantageous Effect of the Invention

As described above, according to the present invention, a blood sampling cartridge is formed with a lancet, a blood collection needle and a blood sensor in an integrated manner, so that it is possible to change the blood collection needle and the blood sensor in a simple manner. Further, the plunger of the blood test apparatus holds the lancet, and so, when the skin is punctured with the blood collection needle, the blood collection needle does not wobble and enables high linearity of movement, so that it is possible to puncture the skin with the blood collection needle stably. Still further, after sampling blood, the blood collection needle can move straight backward from the puncturing part and come to a stop. Therefore, the pain of the patient upon sampling blood can be alleviated to a minimum. That is, the plunger holds the lancet, and so a mechanism for preventing the blood collection needle from puncturing the patient's skin several times or a mechanism for adjusting the depth of puncturing, can be realized in a simple manner. By providing such a prevention mechanism and adjustment mechanism to the blood test apparatus instead of providing them to the blood sampling cartridge, it is possible to realize a smaller and lower-cost blood sampling cartridge.

Further, when the blood sampling cartridge is attached, the blood collection needle is accommodated in a holder, so that the blood sampling cartridge can be changed securely without hurting the patient with the blood collection needle, and the patient does not feel fear. Furthermore, the blood collection needle does not allow direct touch to skin, and so is sanitary. Further, every time a test is performed, the blood sensor and the blood collection needle are changed together, and so the blood collection needle can not be used several times, and there is no fear of infection.

BRIEF DESCRIPTION OF DRAWINGS

FIG. 9D is a cross-sectional view of the blood sensor having a hole provided on a cover in advance for allowing the blood collection needle to pass through;

FIG. 14A is a plan view of the cover formed with transparent material, of the blood sensor (where a hole, which becomes a storing part, is formed);

FIG. 14B is a plan view of the spacer of the blood sensor;

FIG. 14C is a plan view of the substrate of the blood sensor;

FIG. 15 is a perspective plan view of the blood sensor and shows arrangement of electrodes, and the like;

FIG. 16 is a perspective plan view of another example of the blood sensor and shows arrangement of electrodes, and the like;

FIG. 17 is a perspective plan view of still another example of the blood sensor and shows arrangement of electrodes, and the like;

BEST MODE FOR CARRYING OUT THE INVENTION

[An Overview of the Blood Test Apparatus]

The blood test apparatus according to the present invention has: (1) a housing; (2) a measuring circuit that is accommodated in the housing; (3) two or more connectors that are electrically connected to the measuring circuit; (4) an attaching part that is formed in one side of the housing; (5) a plunger that moves back and forth in the housing; (6) a lancet, one end of which is held by the plunger so as to allow the one end to be inserted and removed; (7) a blood collection needle that is attached to the other end of the lancet; (9) a holder that is inserted and fixed inside the attaching part, and inside which the lancet can move; and (10) a blood sensor that is attached to one end of the holder and that has two or more connection electrodes.

Figure 1:
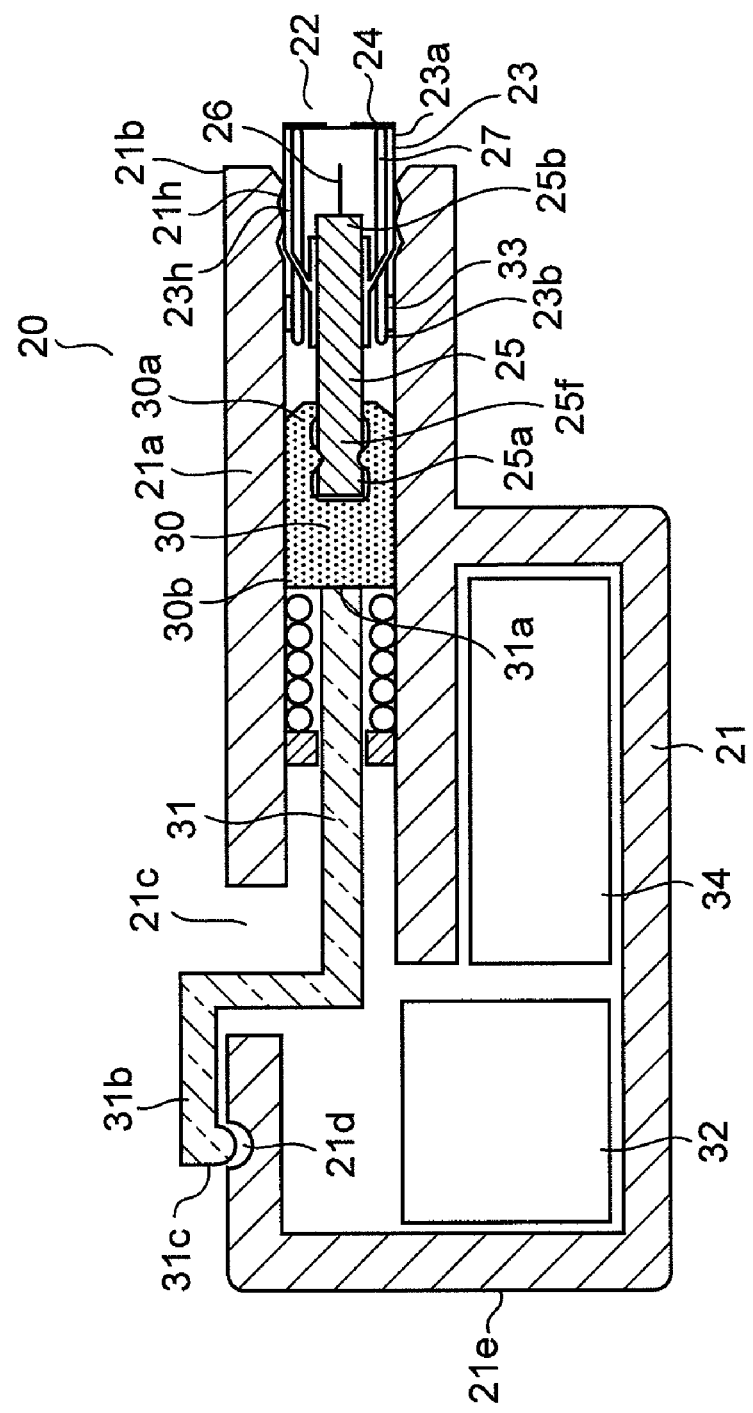
FIG. 1 is a cross-sectional view of a blood test apparatus.

FIG. 1 shows a cross-sectional view of an example of the blood test apparatus of the present invention. Blood test apparatus 20 in FIG. 1 has housing 21 formed with resin. Housing 21 is a frame of the apparatus and accommodates primary members of the apparatus.

Housing 21 accommodates measuring circuit 32. The measuring circuit is a member that receives a detection result of blood components by a blood sensor (described later) and measures the blood components. Information detected by the blood sensor is sent to measuring circuit 32 through connector 27, terminal 33, and the like.

One side of housing 21 is cylindrically-shaped attaching part 21a. Through end 21b of attaching part 21a, blood sampling cartridge 22 is inserted. Positioning concave part 21h provided on the attaching part 21a and positioning convex part 23h provided in holder 23 on the blood sampling cartridge 22 are engaged, and thereby blood sampling cartridge 22 inserted to attaching part 21a is fixed to a predetermined position in attaching part 21a.

Blood sampling cartridge 22 has: cylindrically-shaped holder 23; blood sensor 24 that is attached to one end 23a of holder 23; lancet 25 that can slide in holder 23 freely; and blood collection needle 26 that is attached to the other end 25b of lancet 25. Blood sensor 24 includes a test electrode and a connection electrode connected to the test electrode. Connector 27 contacts with the connection electrode.

Grip part 25f formed near one end 25a of lancet 25 which is one member of blood sampling cartridge 22, is held by holding part 30a provided at one end of plunger 30 that slides inside attaching part 21a. Plunger 30 holds lancet 25, so that, when the skin is punctured with blood collection needle 26, blood collection needle 26 does not wobble and enables high linearity of movement, so that it is possible to puncture the skin with blood collection needle 26 stably.

On the other hand, the other end 30b of plunger 30 is connected to one end 31a of handle 31 formed in the shape of a crank. Latch convex part 31c is formed at the other end 31b of handle 31. Handle 31 goes through hole 21c formed in housing 21 and is latched by the joint of latch convex part 31c and latch concave part 21d.

As the drive mechanism of plunger 30, for example, the method disclosed in Japanese Patent Application Laid-Open No. 2006-314718 can be adopted. According to this method, a puncturing needle can move straight backward and come to a stop after puncturing, so that it is possible to alleviate the pain of the patient upon puncturing to a minimum, and, further, realize a mechanism for preventing the blood collection needle from puncturing the patient's skin several times and a mechanism for adjusting the depth of puncturing, in a simple manner. By providing such a prevention mechanism and an adjustment mechanism on the blood test apparatus, instead of providing on the blood sampling cartridge, it is possible to realize a smaller and lower-cost blood sampling cartridge.

An example of a mechanism for preventing a blood collection needle from puncturing the patient's skin several times, is disclosed in Japanese Patent Application Laid-Open No. 2006-314718.

A pull spring, one end of which is fixed, has the other end hooked on a lever for which rotation is partially limited and which is provided in the plunger. A forward force is given to the plunger by a contracting and restoring force of the pull spring. The plunger moves on by inertia to pass the position where the forward force is no longer given. In this case, the pull spring is extended and the plunger is given a force towards the rear end by the restoring force. In this way, by configuring an urging means that gives a force towards the front end and a force towards the rear end to the plunger, with one pull spring, manufacturing process of a puncturing tool is simplified and a puncturing needle is prevented from puncturing the patient's skin several times (see unexamined patent publication).

Figure 27:
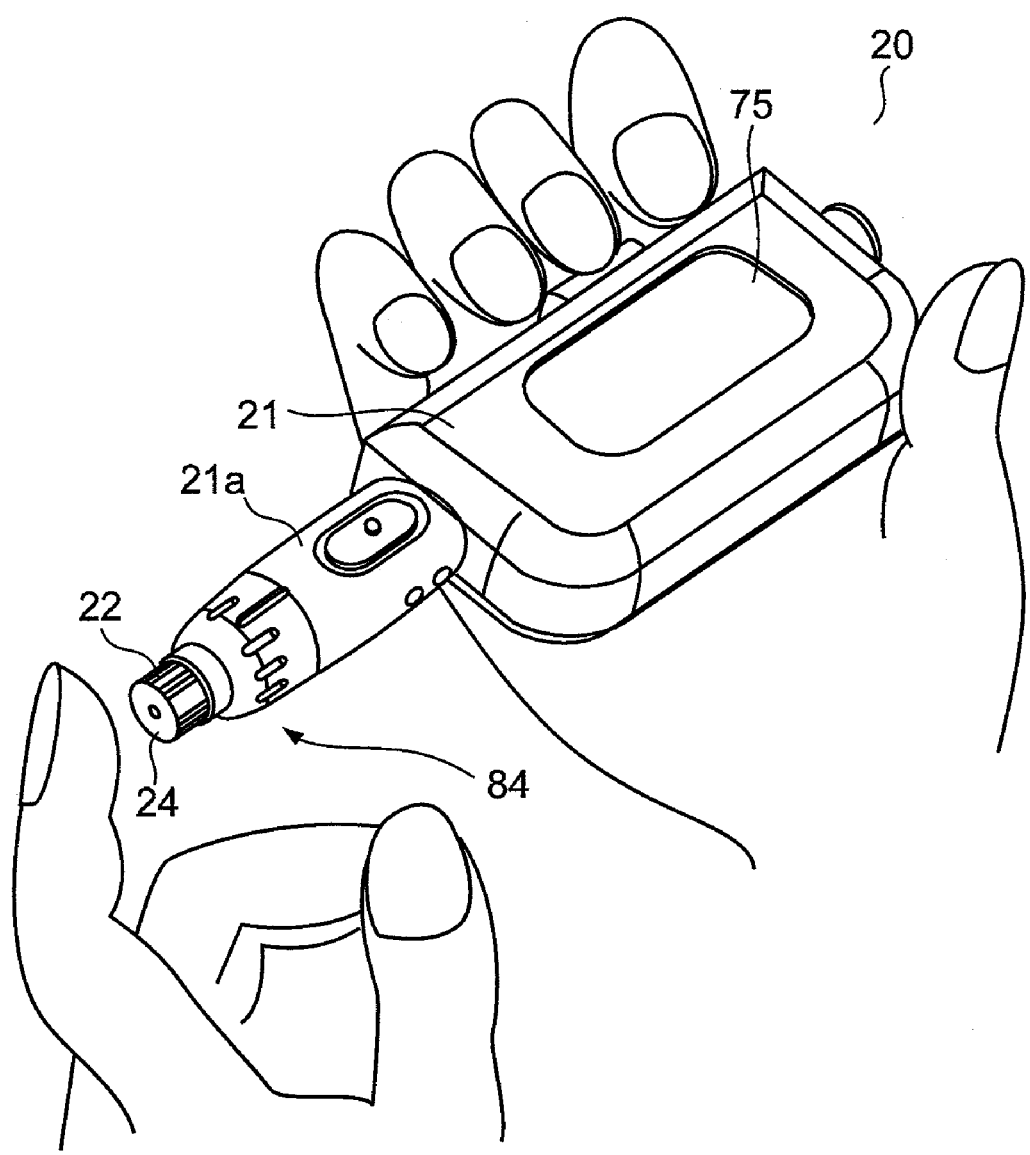
FIG. 27 shows a state of use of the blood test apparatus.
Figure 28:
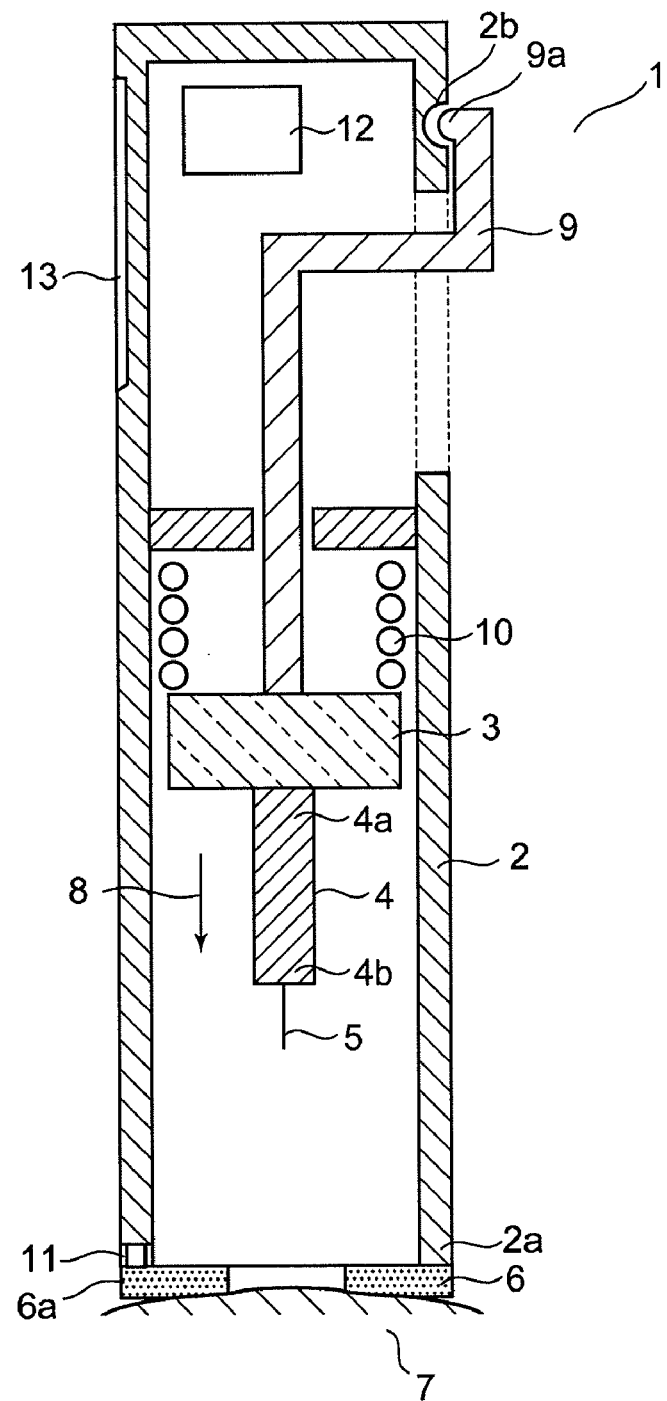
FIG. 28 is a cross-sectional view of the conventional blood test apparatus.

As an example of the mechanism for adjusting the depth of puncturing, when the plunger moves in the direction of the axis, puncturing depth adjusting knob 84 that has a receiving part which limits the amount of the move, is jointed rotatably (see FIG. 27). The receiving part (not shown) of puncturing depth adjusting knob 84 has a helical shape. By rotating adjusting knob 84 with respect to attaching part 21a of housing 21, it is possible to change the amount of the move of the plunger in the direction of the axis.

As described above, measuring circuit 32 is stored inside housing 21 on the other end 21e side. Measuring circuit 32 is connected to terminal 33 formed in attaching part 21a. Further, terminal 33 is connected to connector 27. Terminal 33 is configured with two or more (usually, four or five) terminals 33a to 33d (or 33e) and connected to corresponding connectors 27a to 27d (or 27e). As described above, connectors 27 contact with relevant connection electrodes, respectively.

The housing accommodates battery 34 that supplies power to measuring circuit 32.

As described above, blood test apparatus 20 has blood sampling cartridge 22 that is integrated with built-in lancet 25 with blood collection needle 26 attached and built-in blood sensor 24, and blood sampling cartridge 22 can be attached to and removed from attaching part 21a. Therefore, the whole of blood sampling cartridge 22, including the blood collection needle and the blood sensor, can be changed in a simple manner. Further, blood sensor 24 and blood collection needle 26 are changed together every test, so that there is no fear that blood collection needle 26 is used several times and there is no threat of infection.

Blood collection needle 26 of blood sampling cartridge 22 is accommodated in holder 23 upon attachment, so that blood collection needle 26 does not hurt the patient and is secure and does not make the patient feel fear. Further, blood collection needle 26 accommodated in holder 23 does not allow being touched directly, and so is sanitary.

[The Blood Sampling Cartridge]

FIG. 2 is a diagrammatic perspective view of assembly of an example of a blood sampling cartridge. Blood sampling cartridge 22-1 shown in FIG. 2A has holder 23, blood sensor 24, lancet 25 and blood collection needle 26. Lancet 25 and blood collection needle 26 are formed in an integrated manner so as not to disjoin easily. On the other hand, holder 23 and lancet 25 may be integrated after being manufactured separately, and may be separable from each other.

Figure 2A:
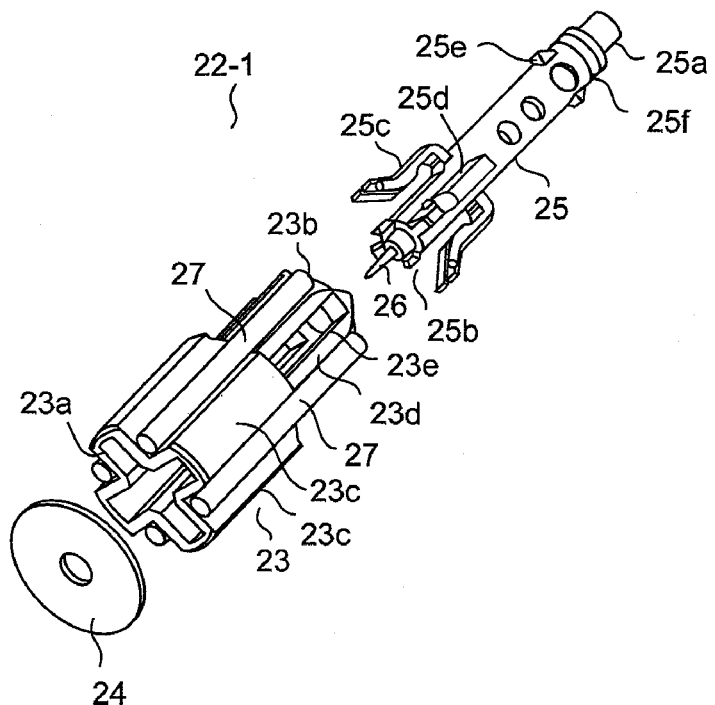
FIG. 2A is an assembly drawing of a blood sampling cartridge forming the blood test apparatus.
Figure 2B:
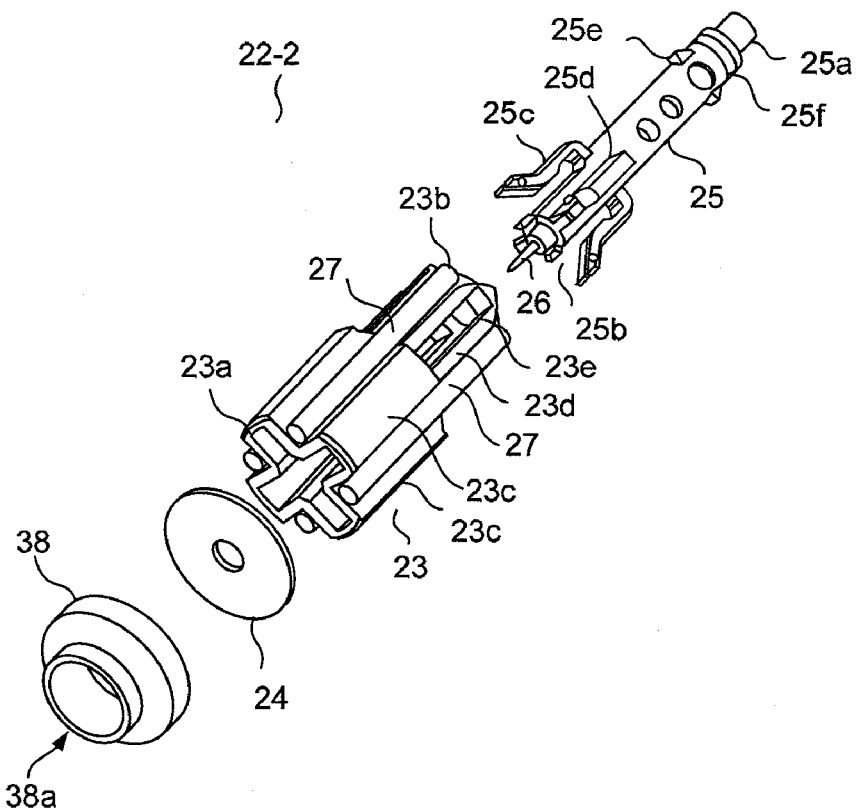
FIG. 2B is an assembly drawing of the blood sampling cartridge having a second holder.
Figure 2C:
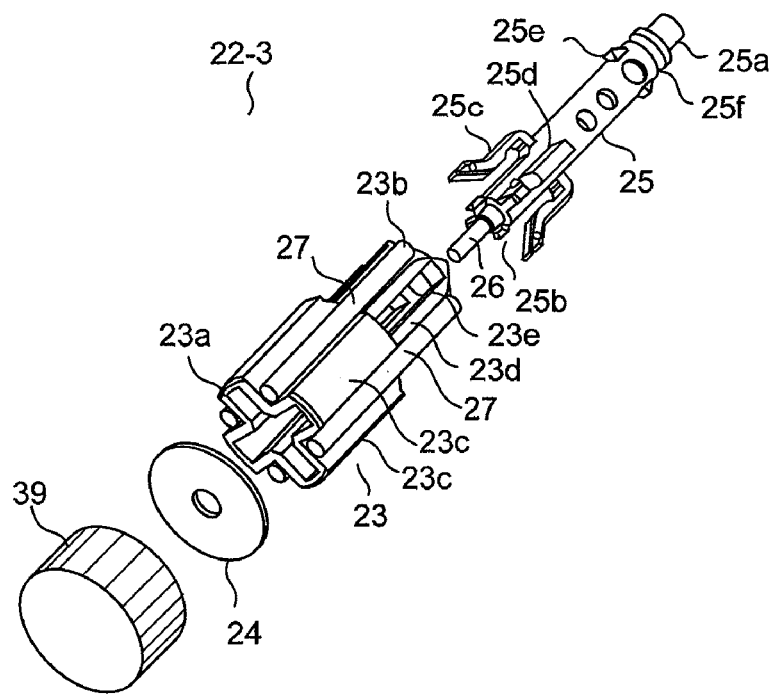
FIG. 2C is an assembly drawing of the blood sampling cartridge having a cap.
Figure 2D:
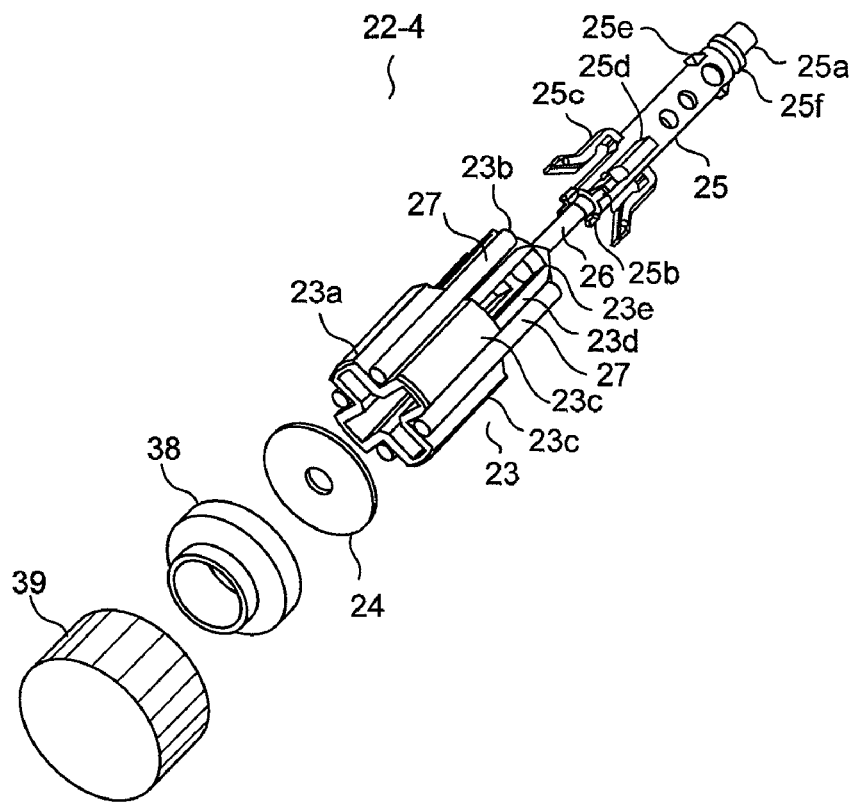
FIG. 2D is an assembly drawing of the blood sampling cartridge having the second holder and the cap.

Blood sampling cartridge 22-2 shown in FIG. 2B further has second holder 38, blood sampling cartridge 22-3 shown in FIG. 2C further has cap 39, and blood sampling cartridge 22-4 shown in FIG. 2D further has second holder 38 and cap 39.

Blood sensor 24 is attached to one end 23a of holder 23 and examines the blood sampled by puncturing using blood collection needle 26.

A cross section of holder 23 on the side where the blood sensor 24 is attached has a cross shape. Connectors 27 (in the blood test apparatus) formed with conductive metal are guided between convex parts 23c of a cross shape, and connectors 27 each contact with the connection electrodes of blood sensor 24. The other end side 23b of holder 23 has convex parts 23d formed integrated with convex parts 23c. Holes 23e are provided at convex parts 23d.

Lancet 25 is inserted in holder 23. Lancet 25 has guides 25c for preventing reuse and guides 25d for improving linearity, which are provided in an integrated manner. As shown in FIG. 2A, two guides 25c and two guides 25d are provided. Each of two guides 25c and each of two guides 25d face each other 180 degrees apart.

Guides 25d of lancet 25 are provided so as to slide in holes 23e provided in convex parts 23d of holder 23. Convex parts 25e are provided near one end 25a of lancet 25. Between convex part 25e and one end 25a, grip part 25f is provided.

Second holder 38 of blood sampling cartridge 22-2 shown in FIG. 2B has circular projecting part 38a abutting on the skin of the patient. Preferably, the inner diameter of projecting part 38a is approximately 4 to 15 mm (more preferably 5 to 7 mm), and the height of the projecting part is approximately 0.5 to 5 mm (more preferably 1 to 2 mm). When projecting part 38a abuts on the skin, the skin is plumped up, so that the blood can be sampled more easily. Further, by applying a negative pressure inside of projecting part 38a, the skin can be in close contact with sensor 24, and so the depth of puncturing using blood collection needle 26 can be adjusted more easily. And projecting part 38a has a circular and projecting shape, so that a negative pressure can be applied reliably. As a result, the blood can be sampled reliably to be brought to the sensor after puncturing.

Although, in FIG. 2B, circular projecting part 38a is provided in the second holder, the projecting part only has to be a concave part that forms space between the skin and blood sensor 24.

Figure 4A:
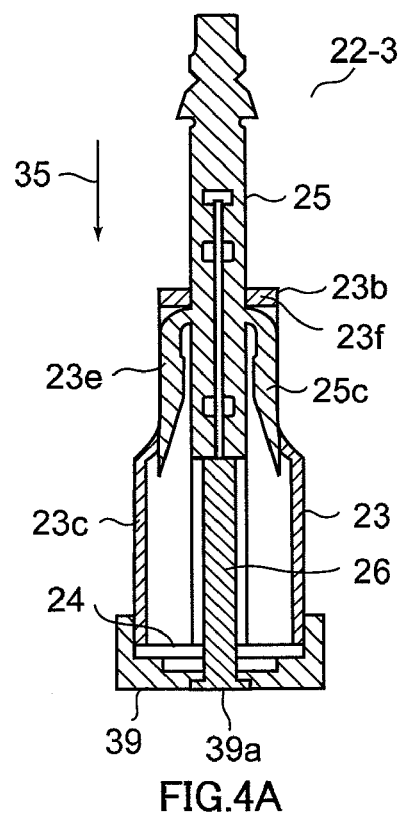
FIG. 4A is a cross-sectional view of the blood sampling cartridge with a cap.

Cap 39 of blood sampling cartridge 22-3 shown in FIG. 2C is used to protect blood sensor 24 and fix lancet 25 of blood sampling cartridge 22-3 before attachment. That is, as shown in FIG. 4A, cap 39 passes through sensor 24 and can be connected to lancet 25. Further, cap 39 can be connected with lancet 25 so as to encompass blood collection needle 26 attached to lancet 25, so that it is possible to keep sterile blood collection needle 26 sanitary.

Further, in case where cap 39 is fixed to lancet 25, when blood sampling cartridge 22-3 is attached to the apparatus, it is possible to attach lancet 25 to holding part 30a (see FIG. 1) in a simple and reliable manner.

Figure 4B:
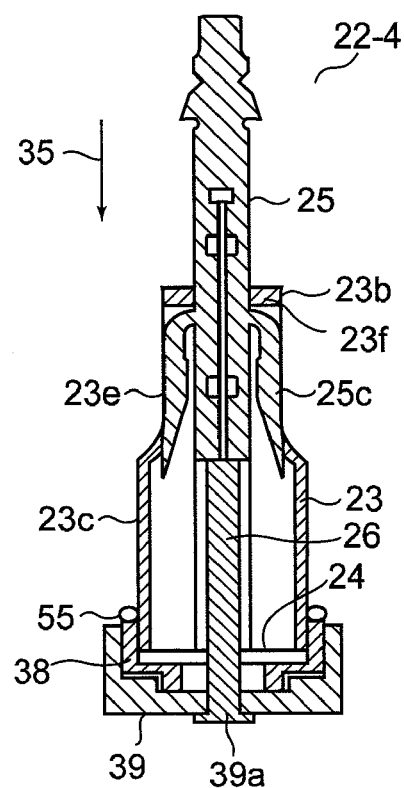
FIG. 4B is a cross-sectional view of the blood sampling cartridge with the second holder and the cap.

Blood sampling cartridge 22-4 shown in FIG. 2D has both second holder 38 included in blood sampling cartridge 22-2 and cap 39 included in blood sampling cartridge 22-3, and so has the benefits of both. FIG. 4B is a cross-sectional view of blood sampling cartridge 22-4.

FIG. 3 is a diagrammatic perspective view of blood sampling cartridge 22.

Figure 3A:
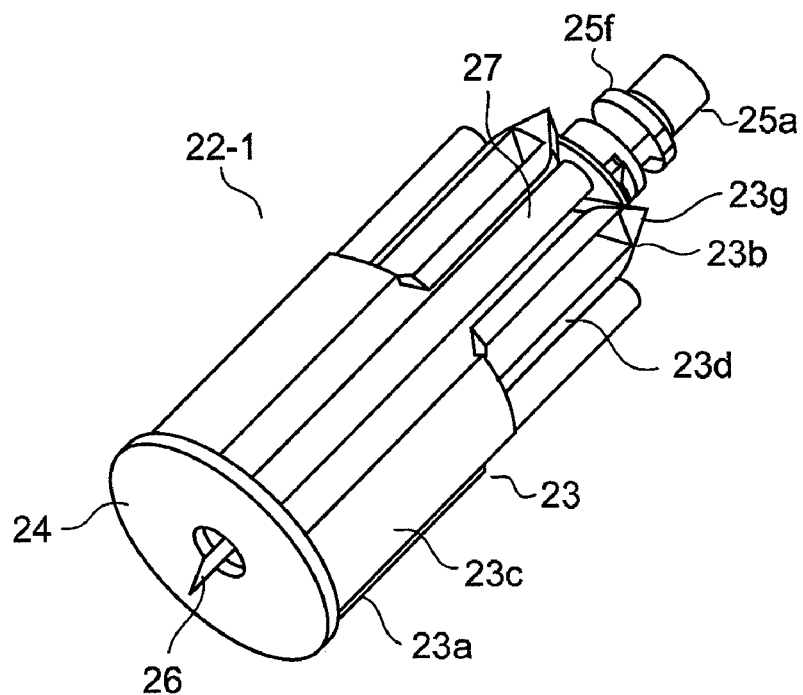
FIG. 3A is a diagrammatic perspective view of the blood sampling cartridge.

In blood sampling cartridge 22-1 shown in FIG. 3A, the height of cross-shaped convex part 23c formed on the one end side 23a (blood sensor side) of holder 23 is higher than the height of cross-shaped convex part 23d formed on the other end side 23b of holder 23. That is, the convex part side 23d of holder 23 is thinner than the convex part side 23c. In this way, the front part of the holder of the blood sampling cartridge with respect to the insertion direction is thinner than the rear part, so that blood sampling cartridge 22 can be inserted to attaching part 21a readily.

Further, tip part 23g on the side 23b of convex part 23d projects at an acute angle. This is important to make sure that connector 27 formed on the attaching part side 21a contacts with a desired position of blood sensor 24.

The whole of blood sampling cartridge 22-1 can be attached to and removed from attaching part 21a, and so blood collection needle 26 and blood sensor 24 can be attached to and removed from attaching part 21a together. Therefore, blood sensor 24 and blood collection needle 26 can be attached and changed in a simple manner.

Figure 3B:
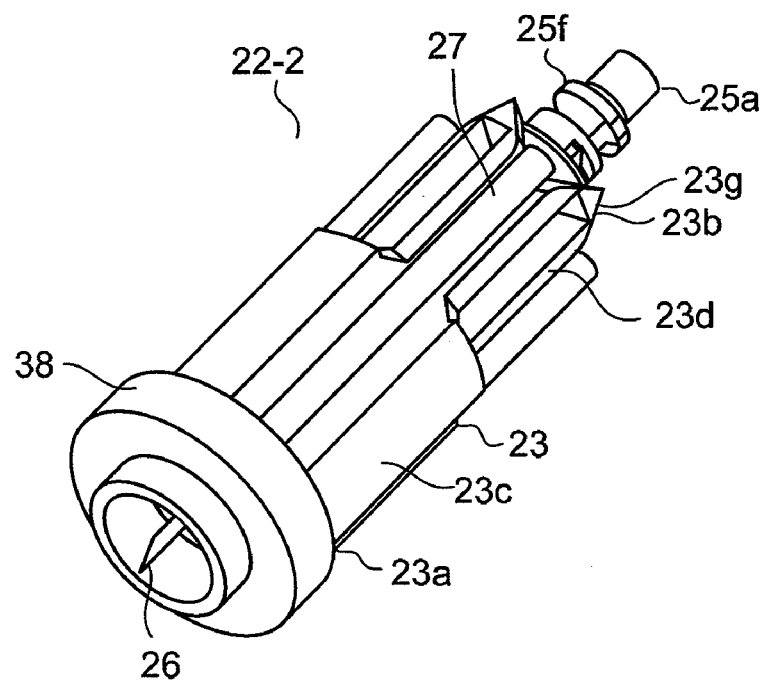
FIG. 3B is a diagrammatic perspective view of the blood sampling cartridge having the second holder.

Blood sampling cartridge 22-2 shown in FIG. 3B is the same as blood sampling cartridge 22-1 shown in FIG. 3A except that blood sampling cartridge 22-2 has second holder 38 (see FIG. 2B) that covers blood sensor 24.

Figure 5A:
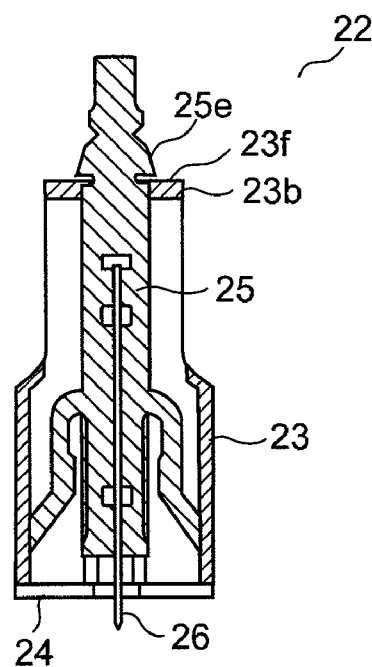
FIG. 5A is a cross-sectional view of the blood sampling cartridge upon puncturing.
Figure 5B:
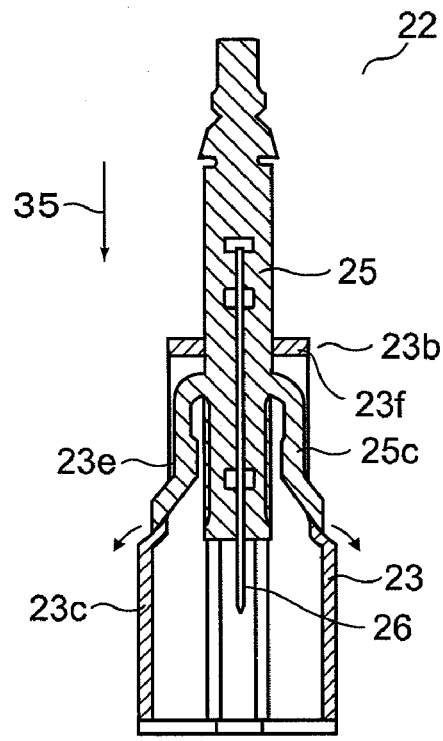
FIG. 5B is a cross-sectional view of the blood sampling cartridge after puncturing is finished.

FIG. 5A is a cross-sectional view of blood sampling cartridge 22 upon puncturing, and FIG. 5B is a cross-sectional view of blood sampling cartridge 22 when puncturing is finished.

As shown in FIG. 5A, upon puncturing, blood collection needle 26 projects from blood sensor 24 and comes to a stop. At this time, convex part 25e of lancet 25 is latched at latch part 23f provided at the other end 23b of holder 23. Therefore, blood collection needle 26 does not project further from the blood sensor. As shown in FIG. 5B, when puncturing is finished, blood collection needle 26 is accommodated in holder 23 and comes to a stop. The roots of guides 25c of lancet 25 are latched at latch part 23f provided at the other end 23b of holder 23. Therefore, lancet 25 does not fall off from holder 23.

In the state shown in FIG. 5B, blood sampling cartridge 22 is removed from attaching part 21a. In the state shown in FIG. 5B, even if lancet 25 is pushed in the direction of arrow 35 by error, guides 25c run onto convex parts 23c from holes 23e of holder 23 by their elasticity. The bases of guides 25c are then latched at the ends of holes 23e and come to a stop, and so blood collection needle 26 does not project from blood sensor 24 again and is secure and does not make the patient feel fear.

Figure 6:
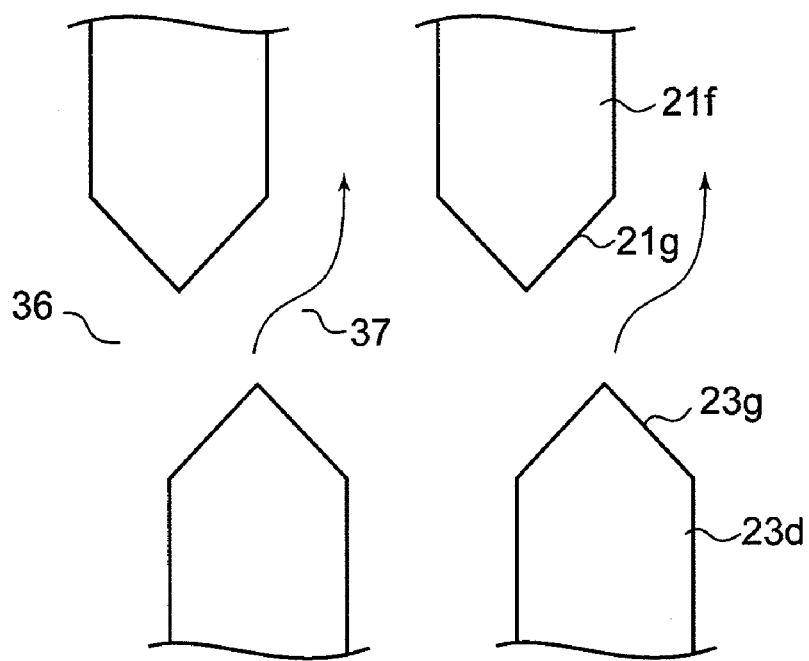
FIG. 6 is a plan view that expands the main part of a guide for inserting the blood sampling cartridge into an attaching part.

FIG. 6 is a plan view that expands the main part of guide 36 for inserting blood sampling cartridge 22 to attaching part 21a. Guide 36 is formed with convex part 21f provided on the internal surface of attaching part 21a and convex part 23d provided on the external surface of the holder. Tip part 21g of convex part 21f and tip part 23g of convex part 23d are preferably formed to have a sharp angle.

Convex part 21f and convex part 23d face each other when blood sampling cartridge 22 is inserted into attaching part 21a, and control the rotation angle with respect to the axis of the direction of inserting the blood sampling cartridge, adequately. That is, when blood sampling cartridge 22 is inserted into attaching part 21a, even when the rotation angle with respect to the axis of the insertion direction, is off from a desired position, as shown by arrow 37, blood sampling cartridge 22 is inserted along guide 36 while the rotation angle with respect to the axis is corrected. By this means, connector 27 provided at attaching part 21a is made to contact with a desired position (contact part of the connection electrode) of blood sensor 24 of blood sampling cartridge 22 reliably.

Figure 7:
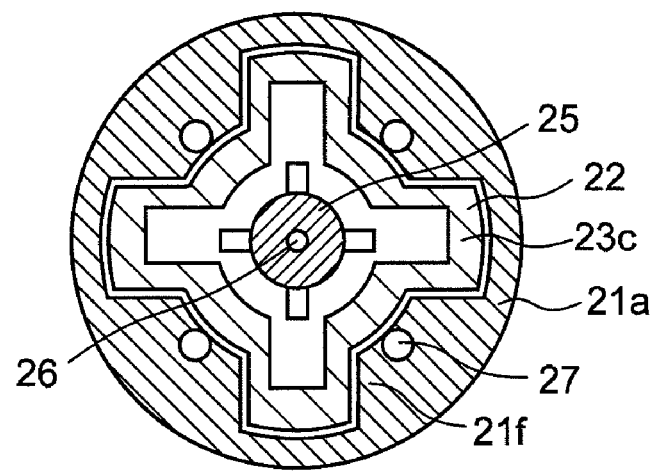
FIG. 7 is a cross-sectional view of the attaching part into which the blood sampling cartridge is inserted.

FIG. 7 is a cross-sectional view showing a state where blood sampling cartridge 22 is attached to inside of attaching part 21a. As described above, blood sampling cartridge 22 is guided by guide 36 and inserted, and, as shown in FIG. 7, convex part 21f and convex part 23c are engaged, and thereby blood sampling cartridge is fixed at a specific angle (angle at which connectors 27 abut on terminals 33) specified in attaching part 21a. This is important to deliver signals of blood sensor 24 to measuring circuit 32 reliably.

The outer periphery of blood sampling cartridge 22 or the inner periphery of attaching part 21a does not have to be round and may be an elliptic or a polygonal. If the outer periphery of blood sampling cartridge 22 or the inner periphery of attaching part 21a is round or regular polygon, blood sampling cartridge 22 can be inserted at an arbitrary rotation angle with respect to the axis of the insertion direction, so that the insertion is facilitated.

It is also possible to make the cross sections of blood sampling cartridge 22 and attaching part 21a asymmetrical and insert blood sampling cartridge 22 only in a fixed direction. For example, it is also possible to form a convex part at part of blood sampling cartridge 22, form a concave groove at attaching part 21a matching the convex part, and fit in the convex part along this groove.

[The State where the Blood Sampling Cartridge is Attached to the Blood Test Apparatus]

Figure 8A:
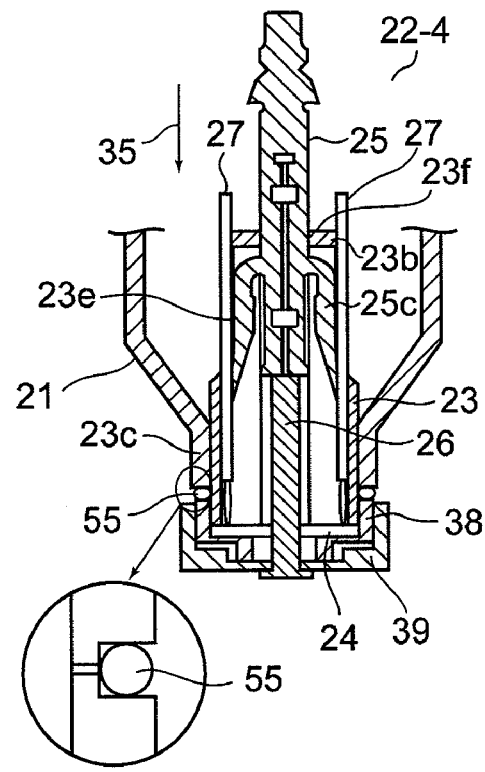
FIG. 8A is a cross-sectional view showing a state where the blood sampling cartridge is attached to the attaching part of the blood test apparatus, particularly, showing a state where a blood sensor of the blood sampling cartridge contacts with a connector of the blood test apparatus; a state where a holder of the blood sampling cartridge and a housing of the blood test apparatus are connected via a sealing material.

FIG. 8A is a cross-sectional view of a state where blood sampling cartridge 22-4 shown in FIG. 4B is attached to attaching part 21a of blood test apparatus 20.

Second holder 38 of blood sampling cartridge 22-4 and housing 21 of blood test apparatus 20 join together via seal material 55. Seal material 55 may be provided in either blood sampling cartridge 22-4 or the blood test apparatus. The airtightness inside the apparatus is improved by seal material 55. By improving the airtightness, upon blood sampling, it is possible to apply a negative pressure (described later) near the puncturing position in the apparatus more simply, sample the blood after puncturing quickly and reliably, improve the stability and reliability of the measuring test, reduce the amount of sampled blood, and reduce the load on the patient substantially.

Further, in FIG. 8A, blood sensor 24 which contacts with connector 27 of the blood test apparatus, is supported by second holder 38, so that the contact pressure between connector 27 and blood sensor 24 becomes stable.

Figure 8B:
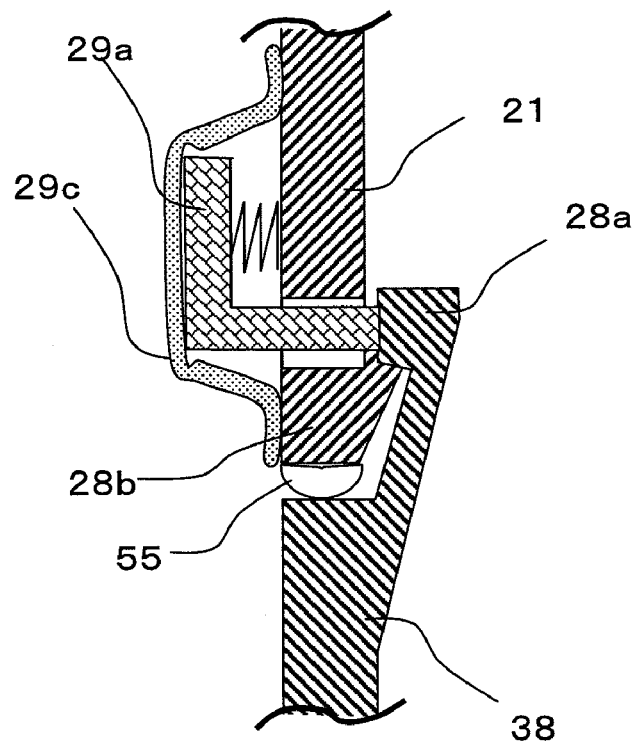
FIG. 8B shows a state in detail where the holder of the blood sampling cartridge and the housing of the blood test apparatus are connected.
Figure 8C:
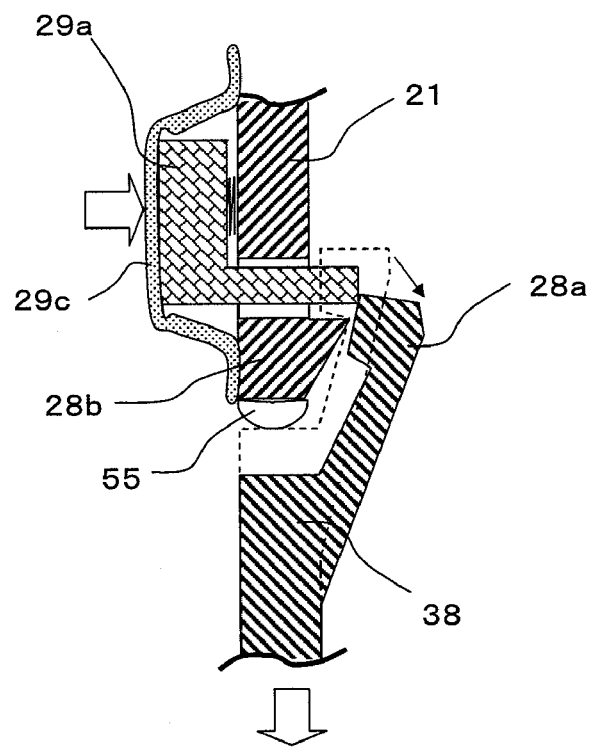
FIG. 8C shows a state in detail where the holder of the blood sampling cartridge and the housing of the blood test apparatus are connected.
Figure 8D:
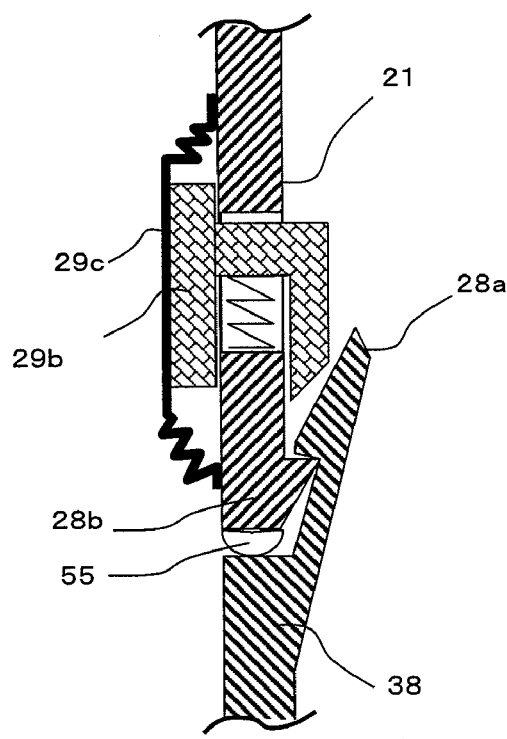
FIG. 8D shows a state in detail where the holder of the blood sampling cartridge and the housing of the blood test apparatus are connected.

In FIG. 8A, seal material 55 is sandwiched between second holder 38 of blood sampling cartridge 22-4 and an end of housing 21 of blood test apparatus 20. On the other hand, FIG. 8B and FIG. 8D show a mechanism of locking blood sampling cartridge 22-4 in housing 21. That is, not only by sandwiching seal material 55, but also by making locking claw (moving side) 28a provided in holder 38 of blood sampling cartridge 22-4 and locking claw (fixed side) 28b provided in housing 21 fit in, blood sampling cartridge 22-4 is locked. A pressure is applied to seal material 55 from both, and the position of blood sampling cartridge 22-4 is thereby fixed, so that the airtightness inside the apparatus improves and the stability improves significantly.

Locking claw 28a on the moving side or locking claw 28b on the fixed side only have to be provided at either holder 38 of blood sampling cartridge 22-4 or housing 21 of apparatus 20, and the same effect can be obtained.

Figure 8E:
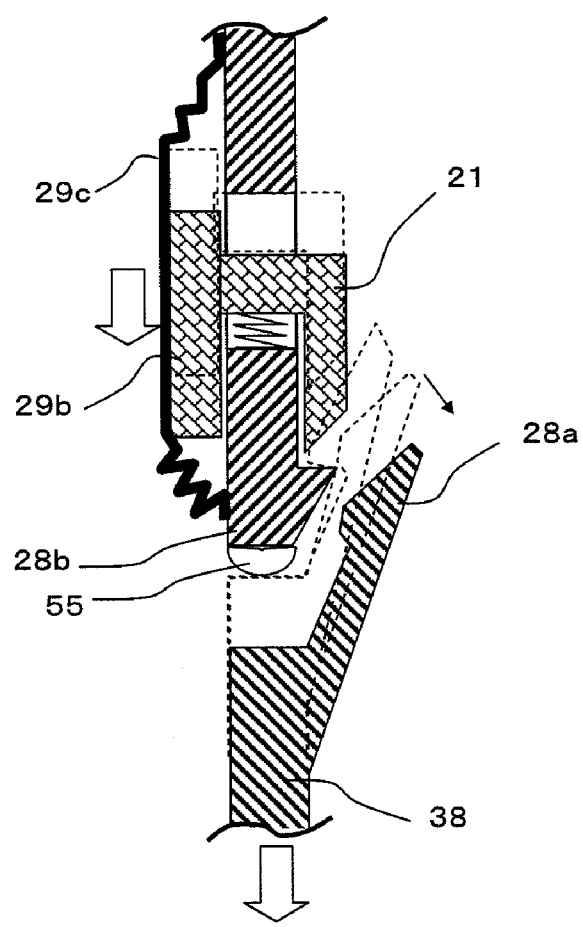
FIG. 8E shows a state in detail where the holder of the blood sampling cartridge and the housing of the blood test apparatus are connected.

Locking is released in a simple manner with, for example, push button 29a (see FIG. 8C) or slide button 29b (see FIG. 8E), provided on the housing 21, and workability of the releasing is good. It is also possible to use electric and pneumatic drive of an electromagnetic valve instead of the push button. Of course, it is also possible to add rubber or other seal material 29c to maintain the seal effect at space and the moving part near the locking member.

[The Blood Sensor]

As described above, blood sampling cartridge 22 has blood sensor 24.

Blood sensor 24 has: a base plate; a storing part provided on the base plate; a supply channel, one end of which communicates with the storing part; a detecting section provided in the supply channel; and an air hole that communicates with the supply channel. One surface of the base plate abuts on the skin to be punctured, and the hole formed on the substrate surface which abuts on the skin is an opening part of the storing part. The blood flowing out from the skin by puncturing is led to the storing part from the opening part.

Figure 9A:
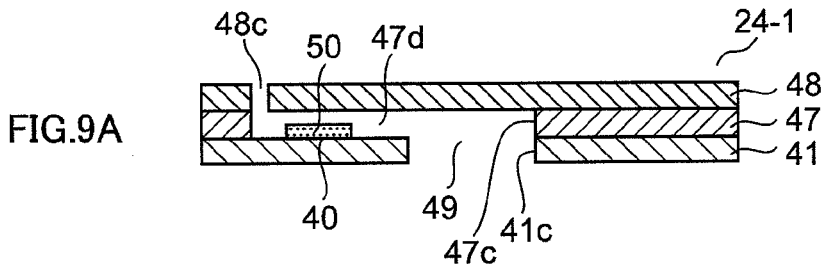
FIG. 9A is a cross-sectional view of the blood sensor.

FIG. 9A is a cross-sectional view of blood sensor 24-1, which is an example of the blood sensor. Blood sensor 24-1 has substrate 41, spacer 47 stacked on the upper surface of substrate 41, and cover 48 stacked on the upper surface of spacer 47. Hole 41c provided in substrate 41 and hole 47c provided in spacer 47 form blood storing part 49. Supply channel 47d is connected to storing part 49. The tip of supply channel 47d is connected to air hole 48c.

Reagent 50 is preferably placed on detecting section 40. Detecting section 40 will be described later, but, for example, is on detection electrodes 42 and 44 (described later) on substrate 41. Reagent 50 is selected as appropriate depending on the type of the blood component to be measured. When the glucose level is measured, reagent 50 is prepared by dropping in the detecting section reagent solution prepared by adding and dissolving PQQ-GDH (0.1 to 5.0 U/sensor), potassium ferricyanide (10 to 200 mM), maltitol (1 to 50 mM) and taurine (20 to 200 mM) to a 0.01 to 2.0 wt % aqueous solution of CMC, and drying the reagent solution.

Figure 9B:
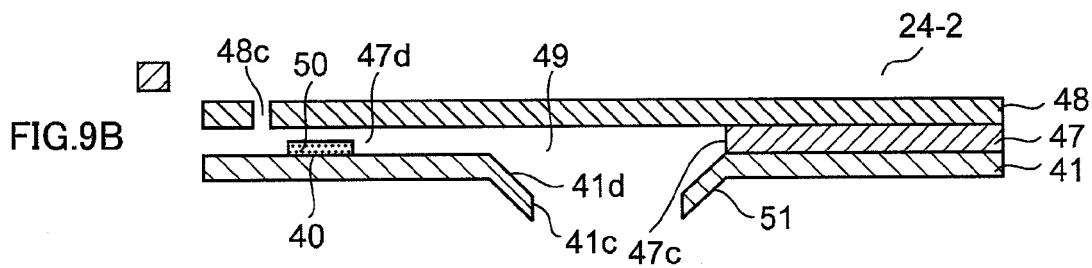
FIGS. 9B and 9C are cross-sectional views of the blood sensor having a bank provided on a substrate.
Figure 9C:
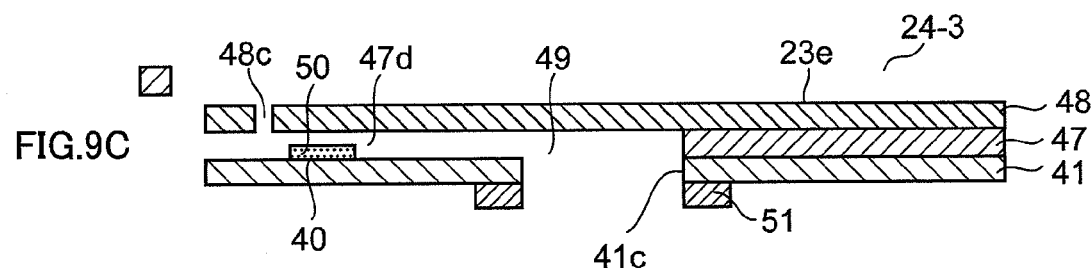

Like blood sensors 24-2 and 24-3 shown in FIGS. 9B and 9C, on the skin contacting surface of substrate 41, bank 51 may be provided near hole 41c. Bank 51 may be formed integrated with substrate 41 by press working, and the like (FIG. 9B), or may be formed with separate members (FIG. 9C). Bank 51 in FIG. 9C may be formed by pasting ring member 54 shown in FIG. 13 to hole 41c. Ring member 54 is pasted so that hole 54a of ring member 54 is continuous with substrate hole 41c forming storing part 49. The diameter of substrate hole 41c forming storing part 49 is preferably the same as the diameter of hole 54a of ring member 54. The other members may be made the same as in blood sensor 24-1.

In FIG. 9B, storing part 49 is formed with lifting part 41d and hole 41c, which are provided in substrate 41, and hole 47c provided in spacer 47.

The height of the bank is preferably 0.5 to 5 mm (more preferably, 1 to 2 mm). Bank 51 prevents sampled blood from flowing out without being led to storing part 49 of the blood sensor.

Figure 9D:
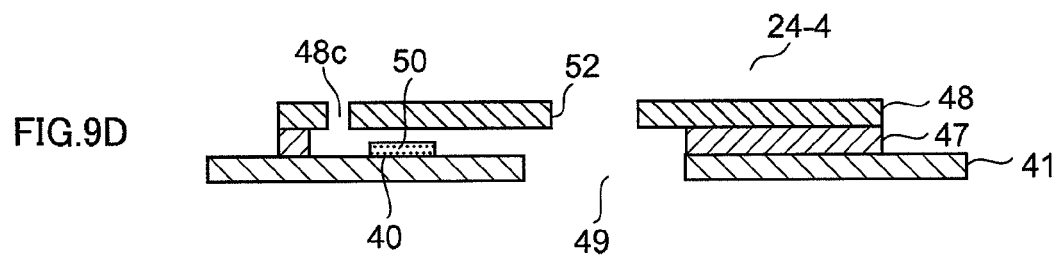

As in blood sensor 24-4 shown in FIG. 9D, hole 52 may be provided in cover 48. Blood collection needle 26 passes through hole 52. When hole 52 is provided in cover 48 in advance, it is not necessary to open a puncturing hole using puncturing needle 26, so that less force is required upon puncturing, and the damage of the needle tip of puncturing needle 26 is minimized.

Figure 9E:
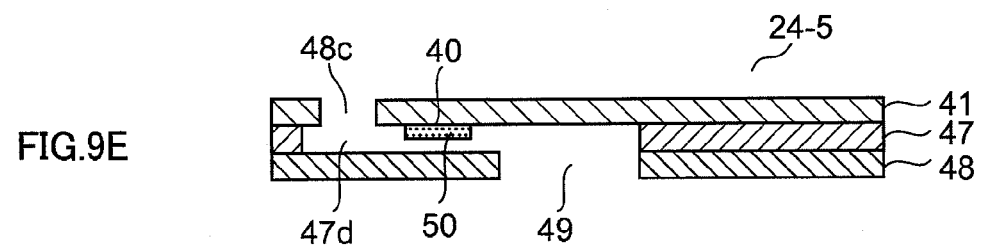
FIG. 9E is a cross-sectional view of the blood sensor, part of the member being formed with a transparent member.

As in blood sensor 24-5 shown in FIG. 9E, it is also possible to form storing part 49 with cover 48 and spacer 47 and form air hole 48c in substrate 41. When cover 48 for blood sensor 24-5 is made a transparent member, it is possible to check whether blood is supplied to supply channel 47d or detecting section 40 from outside.

Figure 10A:
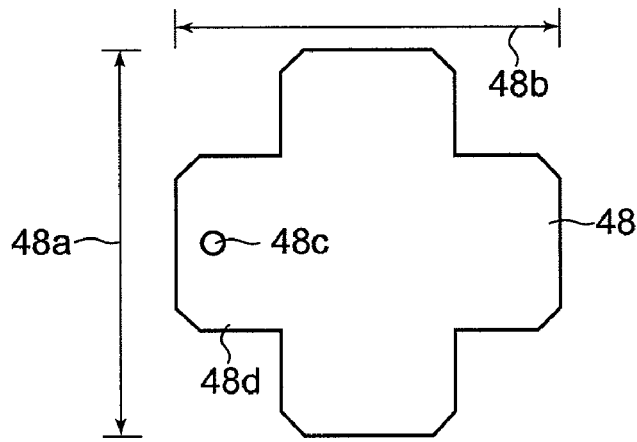
FIG. 10A is a plan view of the cover of the blood sensor.
Figure 10B:
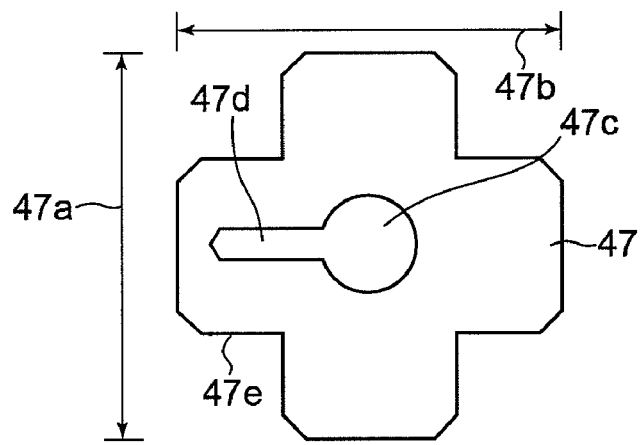
FIG. 10B is a plan view of a spacer of the blood sensor.
Figure 10C:
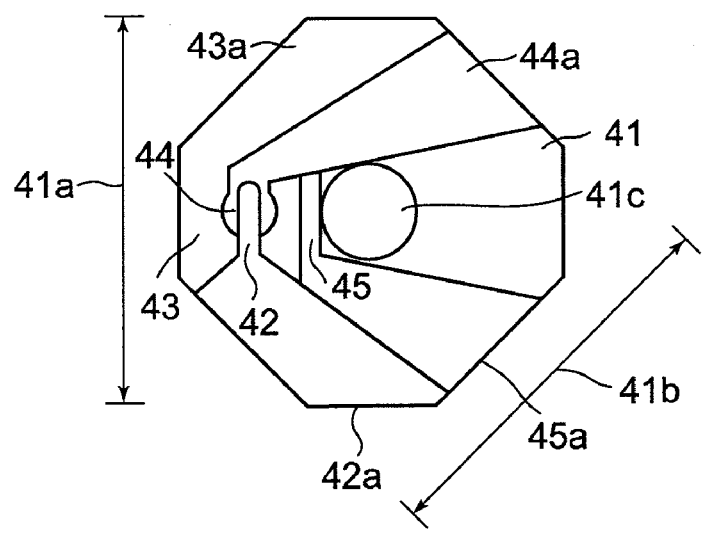
FIG. 10C is a plan view of a substrate of the blood sensor.

FIG. 10 is a plan view that disassembles blood sensor 24. Blood sensor 24 has cover 48 shown in FIG. 10A, spacer 47 shown in FIG. 10B and substrate 41 shown in FIG. 10C.

FIG. 10C is a plan view of substrate 41. Although substrate 41 has an octagon shape, the shape of the substrate is not particularly limited. The material of substrate 41 is preferably resin such as polyethylene terephthalate (PET). The thickness of substrate 41 preferably falls within the range from 0.075 to 0.25 mm (preferably 0.188 mm).

On one surface of substrate 41 (surface that is pasted with spacer 47), detection electrodes 42 to 45 and connection electrodes 42a to 45a connected to detection electrodes 42 to 45, respectively, are formed in an integrated manner. Detection electrodes 42 to 45 and connection electrodes 42a to 45a are formed by forming a conductive layer through the sputtering method or the vapor deposition method, with gold, platinum, palladium as material and applying laser machining to this conductive layer. Hole 41c is provided in approximately the center of substrate 41, and its diameter may be approximately 2.0 mm.

By using transparent material as material of substrate 41, and making the detection electrodes thin transparent films, it is possible to observe the blood in supply channel 47 readily.

FIG. 10B is a plan view of spacer 47. The thickness of spacer 47 may fall in a range of 0.05 to 0.15 mm (preferably 0.1 mm). Spacer 47 is preferably a polygonal (preferably a regular polygon) such as an approximate cross shape, because connector 27 (not shown) can be arranged easily in a dent of the cross-shape. Hole 47c is provided at the position corresponding hole 41c which is provided in approximately the center of spacer 47 on substrate 41. The diameter of hole 47c may be made the same (2.0 mm) as the diameter of hole 41c.

Slit 47*d* is formed in the direction from hole 47*c* to cross-shaped first convex part 47*e* and corresponds to the blood supply channel. By setting the width of the groove of slit 47*d* 0.6 mm and setting the length in the flow channel direction 2.4 mm, the cavity of supply channel 47*d* may be set approximately 0.144 µL. In this way, the test can be performed with a small amount of blood, so that the load on the patient becomes small, and the patient does not feel fear. The material of spacer 47 may be resin such as polyethylene terephthalate (PET).

FIG. 10A is a plan view of cover 48. Cover 48 has an approximate cross shape, air hole 48*c* is provided at cross-shape first convex part 48*d* so as to correspond to the tip part of supply channel 47*d*. Preferably, the diameter of air hole 48*c* is approximately 50 µm.

The material of cover 48 is plastic, and preferably polyethylene terephthalate. The thickness of cover 48 may fall in a range of 0.05 to 0.25 mm (preferably 0.075 mm).

Figure 11A:
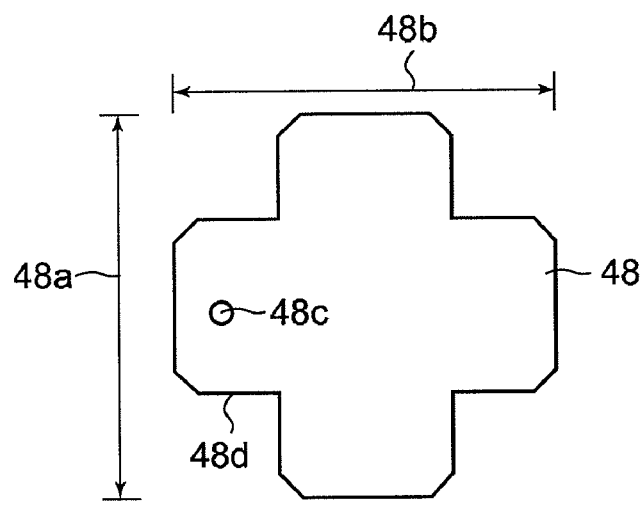
FIG. 11A is a plan view of the cover of the blood sensor.
Figure 11B:
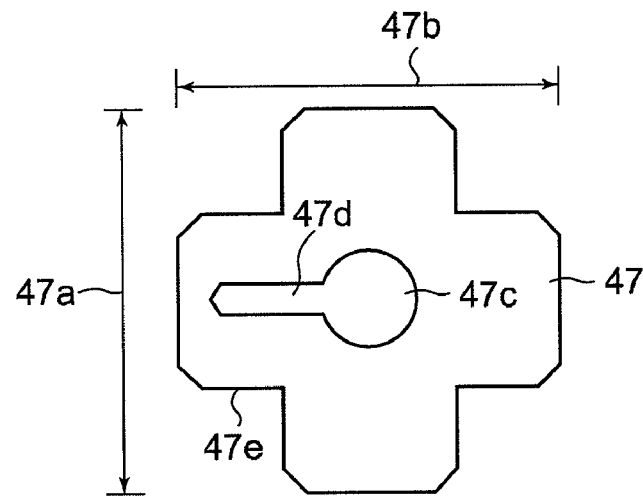
FIG. 11B is a plan view of the spacer of the blood sensor.
Figure 11C:
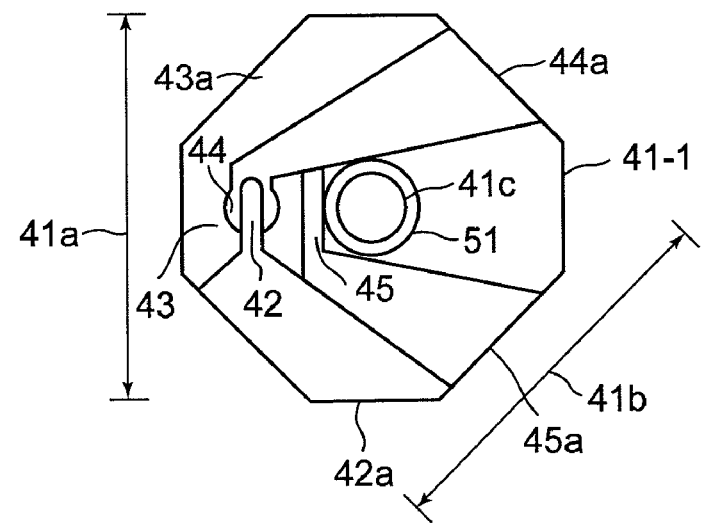
FIG. 11C is a plan view of the substrate of the blood sensor, to which the bank is provided.

FIG. 11 is a plan view that disassembles the blood sensor (see FIG. 9B and FIG. 9C) having a bank. FIG. 11A shows cover 48, FIG. 11B shows spacer 47, and FIG. 11C shows substrate 41-1 on which bank 51 is formed. The blood sensor shown in FIG. 11 is the same as blood sensor 24 shown in FIG. 10 except substrate 41-1, and so substrate 41-1 will be described.

FIG. 11C is a plan view of substrate 41-1 forming blood sensor 24, and substrate 41-1 has an octagon shape. Material of substrate 41-1 is polyethylene terephthalate (PET), and its thickness can fall in a range of 0.075 to 0.25 mm and is preferably 0.188 mm.

Like substrate 41 of FIG. 10C, on the surface of substrate 41-1, detection electrodes 42 to 45, and connection electrodes 42*a* to 45*a* led from detection electrodes 42 to 45, respectively, are formed in an integrated manner. Hole 41*c* is provided in approximately the center of substrate 41-1, and the diameter of hole 41*c* may be 1.5 mm.

Bank 51 is provided around hole 41*c* of substrate 41-1. Blood sensor 24 is made by stacking spacer 47 on the reverse side of the surface where bank 51 is formed, and further, stacking cover 48 on the upper surface of spacer 47.

Figure 12A:
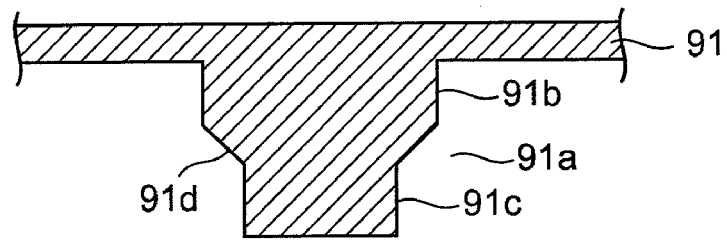
FIG. 12A and FIG. 12B show manufacturing process of the substrate on which the bank is provided.
Figure 12B:
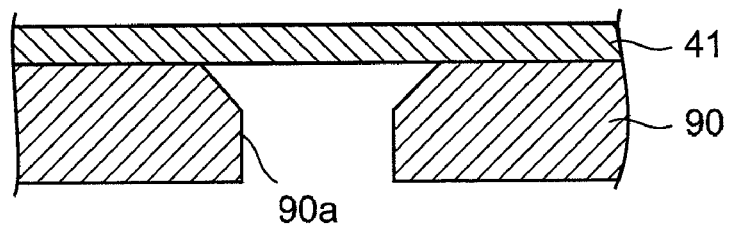
Figure 13:
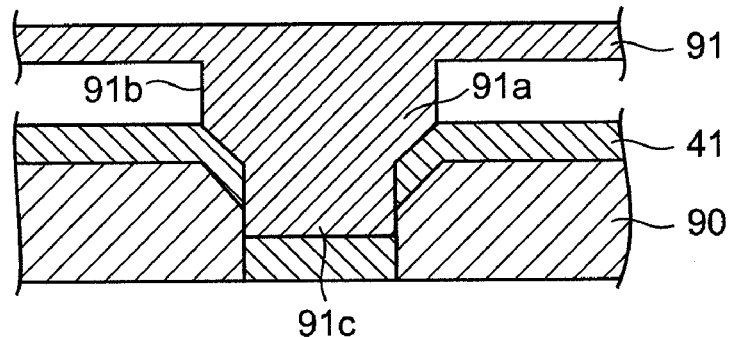
FIG. 13 shows a ring member for forming the bank on the substrate.
Figure 13:
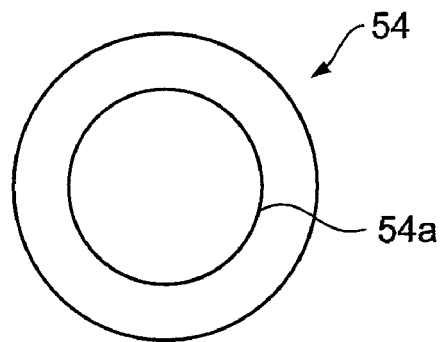

Substrate 41-1 is produced through press working (see FIG. 12), or produced with pasting ring member 54 to substrate 41 (see FIG. 13).

FIG. 12 shows a method of making substrate 41-1 on which bank 51 is formed in an integrated manner, through press working. FIG. 12A shows a state before bank 51 is formed. In FIG. 12A, concave mold 90 has circular hole 90*a*. The diameter of circular hole 90*a* may be approximately 1.55 mm. The upper part of circular hole 90*a* opens upward at an angle of 45 degrees. The diameter of the upper part of the opening part may be approximately 2 mm.

Substrate 41 is mounted on the upper surface of concave mold 90. Further, convex mold 91 is set above substrate 41. On convex mold 91, circular convex part 91*a* that projects downward, is provided. The diameter of base part 91*b* of convex part 91*a* is made approximately 2 mm, and the diameter of tip part 91*c* is made approximately 1.5 mm. Base part 91*b* and tip part 91*c* are connected via 45-degree taper 91*d*. Taper 91*d* forms lifting part 41*d* and bank 51.

By pressing convex part 91*a* of convex mold 91 towards hole 90*a* of concave mold 90, on which substrate 41 is mounted (see FIG. 12B), lifting part 41*d* and bank 51 forming part of storing part 49 can be formed on substrate 41 in an integrated manner.

FIG. 13 shows ring member 54 to be pasted to the lower surface of substrate 41. Ring member 54 has hole 54*a*. It is also possible to stack spacer 47 and cover 48 after forming bank 51 by pasting ring member 54 to substrate 41, or paste member 54 to form bank 51 after stacking substrate 41, spacer 47 and cover 48. The material of member 54 is preferably the same material as substrate 41 or spacer 47 in terms of manufacturing control.

Figure 14A:
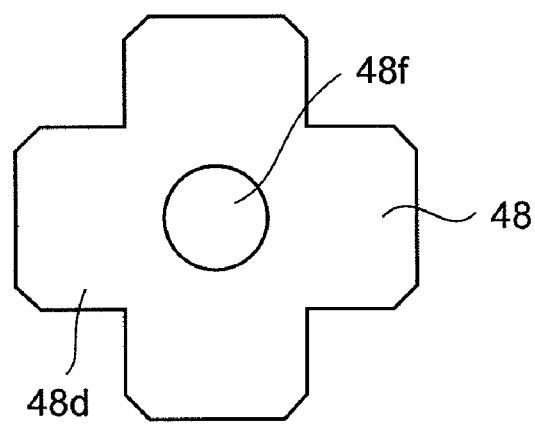
FIGS. 14A, 14B and 14C are plan views that disassemble the blood sensor, part of the base plate being formed with transparent material.
Figure 14B:
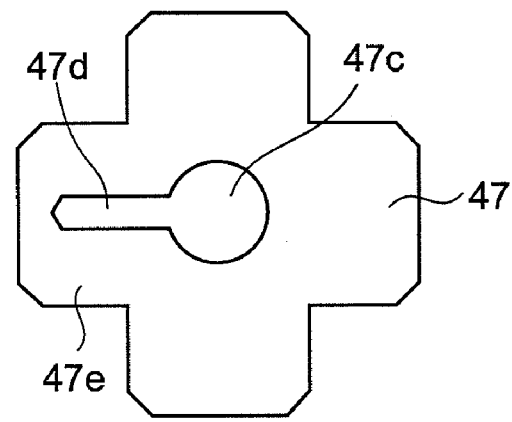
Figure 14C:
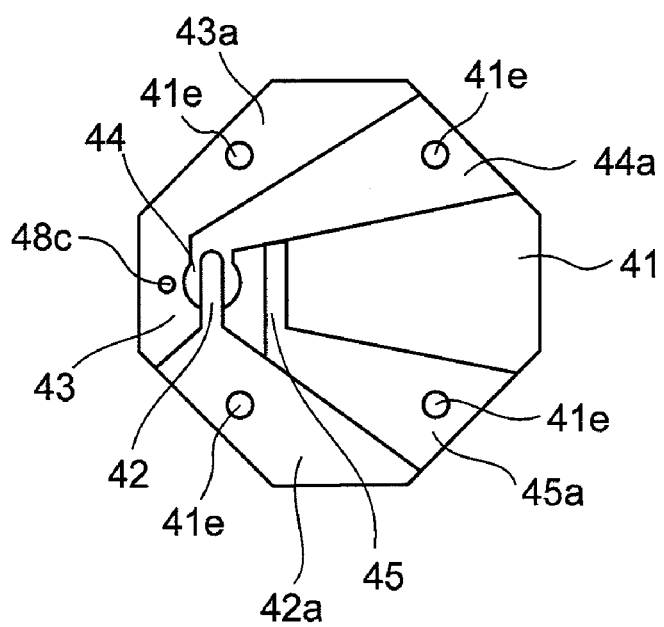

FIG. 14 is a plan view that disassembles blood sensor 24-5 (see FIG. 9E), part of the base plate being formed with a transparent member. FIG. 14A shows cover 48, FIG. 14B shows spacer 47, and FIG. 14C shows substrate 41.

In blood sensor 24-5 shown in FIG. 9E, substrate 41, spacer 47 and cover 48 are placed upside down with respect to blood sensor 24-1 shown in FIG. 9A. Therefore, detection electrodes are formed on the upper side of storing part 49, on substrate 41 shown in FIG. 14C. Hole 41*e* is provided at substrate 41, and connection electrode 43*a* passes through hole 41*e* from detection electrode 43 and is led to the opposite side of the surface in contact with the skin. Further, air hole 48*c* is also provided in substrate 41.

FIG. 14B shows spacer 47 and is the same as FIG. 10B.

FIG. 14A shows cover 48, and its material is preferably transparent material. When cover 48 is transparent, the blood sampled from the skin to the supply channel can be seen, which makes judgment as to whether or not the blood sampling cartridge is used more easily. In the center of cover 48, hole 48*f*, which is part of the storing part, is formed.

[The Thickness of the Substrate, Spacer and Cover]

The thickness of substrate 41, spacer 47 and cover 48 of blood sensor 24, and its ratio are important for sampling the blood. First, to cause the capillary action in supply channel 47*d*, the thickness of the spacer preferably falls within the range from 0.05 to 0.15 mm (preferably 0.1 mm).

Further, with blood sensors 24-1 to 24-4 shown in FIG. 9A to FIG. 9D, to adjust the volume of storing part 49 and supply channel 47, it is necessary to adjust the thickness of spacer 47 and the thickness of substrate 41. The thickness of the substrate is preferably the same as the thickness of the spacer or greater, and preferably falls within the range where the thickness of substrate 41:the thickness of spacer 47=1:1 to 5:1 (preferably, 2.5:1). Further, the thickness of cover 48 is preferably made less than the thickness of substrate 41 so that the total thickness of blood sensor 24 is preferably made thin. Therefore, the thickness of substrate 41:the thickness of spacer 47:the thickness of cover 48 may be 2.5:1.3:1 as a reference.

The term "the thickness of substrate 41" refers to the thickness of cover 48 of blood sensor 24-5 shown in FIG. 9E, and the term "the thickness of cover 48" refers to the thickness of substrate 41 of blood sensor 24-5 shown in FIG. 9E.

[The Relationship Between the Volume of the Blood Storing Part and the Volume of the Blood Supply Channel]

As described above, blood sensor 24 has blood storing part 49 and blood supply channel 47*d*, and the volume of blood storing part 49 is one to twenty times the volume of blood supply channel 47*d*, preferably four to fifteen times, and, more preferably, five to seven times. For example, the volume of blood storing part 49 of blood sensor 24-1 shown in FIG. 9A may be 0.904 µL, and the volume of blood supply channel 47*d* may be 0.144 µL. Further, the volume of blood storing part 49 of blood sensor 24-2 shown in FIG. 9B may be 0.766 µL, and the volume of blood supply channel 47*d* may be approximately 0.144 µL. In this way, by controlling the volume ratio between blood storing part 49 and blood supply channel 47*d* adequately, the speed of the blood flowing in the supply channel can be controlled to be constant and the flow rate of the blood flowing in the supply channel can be controlled adequately, so that the blood does not wash out reagent 50 and reacts with reagent 50 sufficiently, which realizes a correct test.

Further, by controlling the volume ratio between blood storing part 49 and blood supply channel 47d, it is possible to reduce their volumes. Therefore, the amount of the blood sampled for a test can be reduced, and the load on the patient can be also reduced.

[The Relationship Between the Area of the Air Hole and the Area of the Puncturing Hole]

The diameter of air hole 48c is preferably 50 to 500 μm (for example, 50 μm). If the diameter of air hole 48c is made small, blood sampled excessively is less likely to flow out from air hole 48c. Further, the area of air hole 48c is preferably made smaller than the area of puncturing hole 48e formed by blood collection needle 26. When the area of air hole 48c is made larger than the area of puncturing hole 48e, the resistance of puncturing hole 48e against the flow of blood 23 becomes smaller than the resistance of air hole 48c. Therefore, most of blood 13 sampled excessively flows out from puncturing hole 48e, and the amount of blood 13 flowing out from air hole 48c becomes extremely small. Accordingly, even if the blood is sampled excessively, reagent 50 is not washed out. That is, reagent 50 does not move from detecting section 40, and the components of blood 13 are examined correctly.

Further, preferably, the diameter of air hole 48c is smaller than the diameter of blood collection needle 26 and approximately 10 to 80%, and, more preferably, approximately half.

Further, like blood sensor 24-4 shown in FIG. 9D, also in a case where hole 52 is formed in cover 48 in advance, the area of hole 52 is preferably larger than the area of air hole 48c. Further, the area of hole 52 is preferably smaller than the area of hole 41c formed in substrate 41.

[The Relationship of Water-Repellency and Hydrophilicity in the Parts of the Blood Sensor]

First, the reverse side of cover 48 (the surface pasted to the spacer) corresponding to "the inner surface of supply channel 47d" is preferably subjected to hydrophilicity treatment to make the blood smoothly flow in supply channel 47d by capillary action. Further, the reverse side of cover 48 corresponding to "the upper side of storing part 49" is preferably less hidrophilic than the reverse side of cover 48 corresponding to the inner surface of supply channel 47d to make the blood more smoothly flow in supply channel 47d.

The surface of cover 48 (the reverse side of the surface pasted to the spacer) is preferably subjected to water-repellency treatment to prevent the blood in storing part 49 from flowing out more than necessary from air hole 48c or a hole of cover 48 (for example, puncturing hole 48e by blood collection needle 26). Further, the reverse side of cover 48 corresponding to "the upper side of storing part 49" is preferably less water-repellent than the surface of cover 48 to prevent more effectively the blood in storing part 49 from flowing out.

In the surface of substrate 41 which abuts on the skin, at least the periphery of hole 41c is preferably water-repellent, and the whole surface may be water-repellent. The term "water-repellency" preferably refers to a state where the surface free energy is less than 43 mN/m. When the surface of substrate 41 which abuts on the skin is water-repellent, the blood sampled by puncturing the skin with blood collection needle 26 can be brought to storing part 49 more easily.

Further, in blood sensors 24-2 and 24-3 shown in FIG. 9B and FIG. 9C, the wall surface of hole 41c and lifting part 41d are preferably less hydrophilic than supply channel 47d and less water-repellent than the surface of cover 48 (the reverse side of the surface pasted to the spacer).

The level of the hydrophilicity or water-repellency is adjusted by performing hydrophilicity treatment or water-repellency treatment.

To improve the hydropilicity or water-repellency, it is only necessary to mix hydrophilic material or water-repellent material in the material of member constituting the blood sensor or apply hydrophilic material or water-repellent material to the surface of the member. By adjusting the amount of the hydrophilic material or water-repellent material to be mixed or applied, the level of hydrophilicity or water-repellency is also adjusted.

Further, by dissolving or removing hydrophilic material applied on the surface of hydrophobic material (plastic, for example, polyethylene terephthalate), the hydrophilicity can be reduced. Still further, the activity of the hydrophilic material can be adjusted by radiating UV.

Blood sensor 24 for which the hydrophilicity or the water-repellency is controlled as described above is manufactured with, for example, the following method. In advance, water-repellent treatment is applied to the upper surface of cover 48, and hydrophilic treatment is applied to the lower surface of cover 48. Further, in advance, the whole or the periphery of hole 41c of the reverse side of substrate 41 (reverse side of the surface pasted to the spacer) may be subjected to hydrophobic treatment. Next, substrate 41, spacer 47 and cover 48 are stacked (spacer 47 is stacked on the surface of cover 48, where hydrophilicity treatment is applied).

[The Arrangement of Electrodes in the Blood Sensor]

Figure 15:
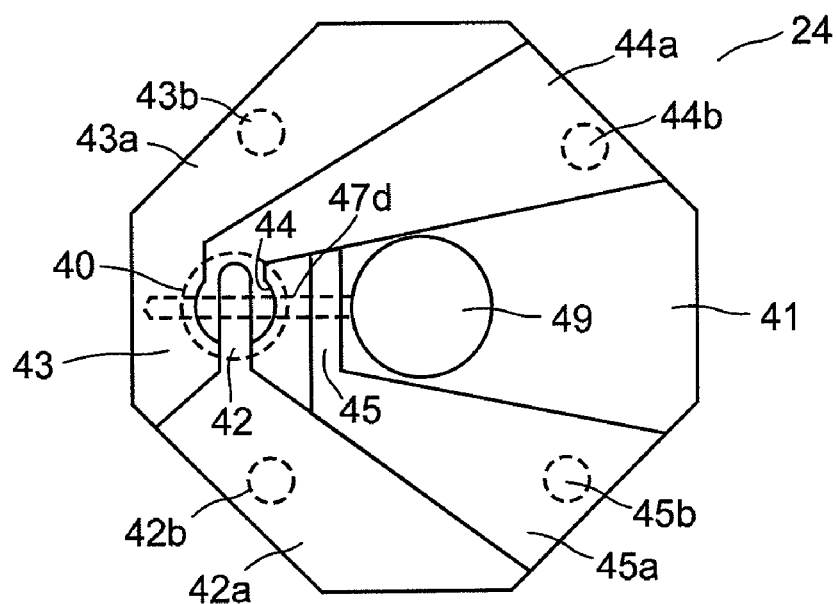

FIG. 15 is a perspective plan view of blood sensor 24. Detection electrodes 42, 43, 44 and 45 are formed on substrate 41, and these detection electrodes 42 to 45 function as, for example, an active electrode, a sensing electrode, a counter electrode and an Hct electrode, in that order. The "active electrode" refers to an electrode for measuring blood components, the "sensing electrode" refers to an electrode for sensing whether or not the blood is supplied to the detecting section, the "counter electrode," refers to a counterpart electrode of the active electrode, and the "Hct electrode" refers to an electrode for measuring the hematocrit level in the blood. Detection electrodes 42 to 45 are connected to relevant connection electrodes 42a, 43a, 44a and 45a, respectively, and connection electrodes 42a, 43a, 44a and 45a are arranged along the outer periphery of substrate 41.

Detecting section 40 is included on substrate 41, and the reagent contacts with detecting section 40. Detecting section 40 preferably includes detection electrode 42 which functions as an active electrode and detection electrode 44 which functions as a counter electrode, and, on the other hand, preferably does not include detection electrode 45 which functions as an Hct electrode.

The blood flowing out from the skin punctured with blood collection needle 26 is brought to storing part 49. The blood brought to storing part 49 flows in supply channel 47d by capillary action, is led by detecting section 40, and reacts with regent 50 in detecting section 40. The result of the reaction is led to connection electrodes 42a, 43a, 44a and 45a connected to the detection electrodes, respectively.

Further, the result of the reaction is led to terminals 33a, 33b, 33c and 33d formed at attaching part 21a via connectors 27a, 27b, 27c and 27d which contact with connection electrodes 42a, 43a, 44a and 45a. And further, the result of the reaction is led to measuring circuit 32 from terminals 33a to 33d.

As shown in FIG. 15, connection electrodes 42a to 45a have contact parts 42b to 45b, respectively, to contact with the connectors. Contact parts 42b, 43b, 44b and 45b contact with connectors 27a, 27b, 27c and 27d, respectively. Contact parts 42b, 43b, 44b and 45b are preferably arranged around a specific point so as to surround the specific point and arranged at equiangular intervals centered on the specific point.

The "specific point" is preferably in storing part 49 (inside hole 41c) on the surface of the substrate, and, more preferably, near the center of storing part 49. Further, the "specific point" may be on the surface of the substrate and on the axis where puncturing needle 26 moves. Still further, the specific point is preferably near the rotation center of the axis of the insertion direction for attaching the blood sampling cartridge to the attaching part, of the blood sampling cartridge.

Further, contact parts 42b to 45b are preferably arranged at approximately the same distance from the specific point.

In this way, connector 27 of the test apparatus contacts with blood sensor 24 at equiangular intervals centered on the specific point, so that the connector and the blood sensor can be connected adequately regardless of the angle at which the blood sampling cartridge is attached. Therefore, the blood sampling cartridge can be attached more readily.

As shown in FIG. 2 described above, by arranging each of connectors 27a to 27d between cross-shape convex parts 23c or 23d formed on the outer periphery of holder 23, the contact parts can be arranged at equiangular intervals centered on the barycentric point of the cross shape of the holder.

In case that contact parts 42b, 43b, 44b and 45b are arranged at equiangular intervals centered on the specific point, when blood sampling cartridge 22 is attached to attaching part 21a and the contact parts contact with the connectors, each of the contact parts can contact with one of the connectors respectively even if the rotation angle with respect to the axis of the insertion direction of the blood sampling cartridge is arbitrary. On the other hand, it is not clear which connectors contact with which contact parts. Therefore, to insert readily the cartridge regardless of the rotation angle with respect to the axis of the insertion direction, a "reference electrode" is preferably provided for specifying which contact parts of the connection electrodes contact with which connectors.

Figure 16:
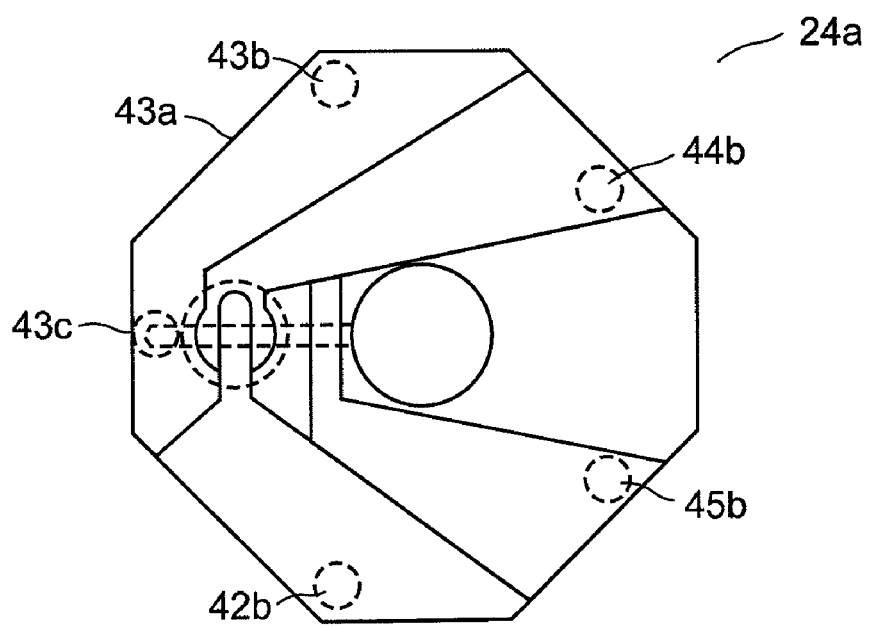

FIG. 16 shows an example where blood sensor 24 has a reference electrode. Blood sensor 24a shown in FIG. 16 has the "reference electrode" for specifying the positions of the connection electrodes in addition to connection electrodes 42a to 45a, as one of the connection electrodes. Blood sensor 24a may be the same as blood sensor 24 shown in FIG. 15 except that the reference electrode is provided. The reference electrode shown in FIG. 16 is reference contact part 43c, which is the position that contacts with the connector. Reference contact part 43c is provided in connection electrode 43a together with contact part 43b, that is, contact part 43b and reference contact part 43c are connected via a conductor. Therefore, the resistance between contact part 43b and reference contact part 43c is zero. Reference contact part 43c may be provided in one of connection electrodes 42a to 45a, and not always necessary provided in connection electrode 43a.

Contact parts 42b to 45b and reference contact part 43c are preferably provided near the outer periphery of blood sensor 24a, arranged around the specific point and arranged at equiangular intervals centered on the specific point. Therefore, five connectors 27 of attaching part 21a are provided at equiangular intervals centered on the specific point so as to correspond to contact parts 42b to 45b and reference contact part 43c, respectively. The holder in this case does not have the cross shape shown in FIG. 2 and preferably has a star shape or the shape of a pentagon, and connectors 27 are provided around the star-shaped or pentagon-shaped holder at the same angle.

By providing reference contact part 43c in addition to contact parts 42a to 45b, even if blood sampling cartridge 22 is inserted into attaching part 21a at an arbitrary rotation angle with respect to the axis of the insertion direction, (A) one of the connectors can contact with one of the contact parts or the reference contact part, and (B) measuring circuit 32 can detect neighboring electrodes between which the electrical resistance is zero, specify connection electrodes including the reference contact part, specify the positions of connection electrodes 42a to 45a, and further specify the functions of the detection electrodes connected to the connection electrodes.

Figure 17:
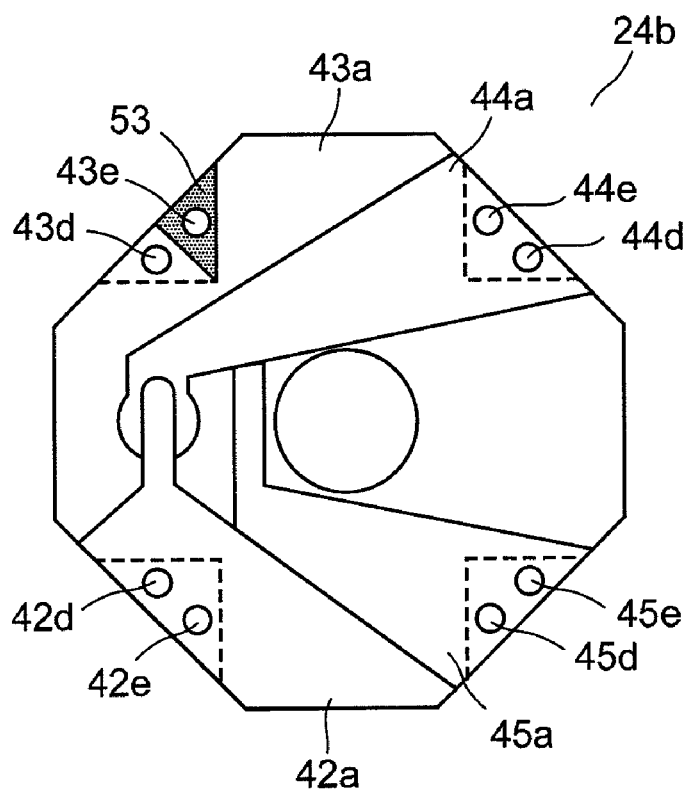

FIG. 17 shows another example where blood sensor 24 has a reference electrode. Connection electrodes 42a to 45a of blood sensor 24b shown in FIG. 17 each have a contact part that contacts with a pair of two connectors. That is, connection electrode 42a has contact parts 42d and 42e, connection electrode 43a has contact parts 43d and 43e, connection electrode 44a has contact parts 44d and 44e, and connection electrode 45a has contact parts 45d and 45e. Only contact part 43e out of contact parts 43d and 43e is formed on insulating member 53. Therefore, 43d and 43e are electrically insulated and the resistance between 43d and 43e becomes infinite, while the resistance between 42d and 42e, 44d and 44e, 45d and 45e becomes zero. To electrically insulate 43d and 43e, 43d may be arranged on insulating member 53 provided on connection electrode 43a, or 43d and 43e may be insulated by providing a slit around 43d.

In this way, 43e insulated from 43d can be used as the reference contact part of the reference electrode. When the electrical resistance between the contact parts in pairs is measured, the resistance in one pair is infinite, so that it is possible to specify reference contact part 43e. Using the specified reference contact position as a reference, the connection electrodes can be identified as connection electrode 43a, connection electrode 44a, connection electrode 45a and connection electrode 42a, clockwise, for example, and the functions of the detection electrodes connected to the connection electrodes can be specified.

Even if cartridge 22 to which the blood sensor (illustrated in FIG. 16 and FIG. 17) is attached, is inserted to attaching part 21a of the blood test apparatus at an arbitrary rotation angle with respect to the axis of the insertion direction, connection electrodes 42a to 45a included in the blood sensor can be specified. Therefore, it is not necessary to adjust and correct the insertion direction of the cartridge by visual checking, so that the insertion becomes simple.

It is also possible to design blood sampling cartridge 22 so as not to be inserted unless the rotation angle with respect to the axis of the insertion direction is a specific angle, and make the specific connectors contact with the specific contact parts. For example, convex part 21f and convex part 23d of the guide shown in FIG. 6 do not have to be provided at regular intervals, but may be provided at different intervals.

Further, a groove (or a convex part) that runs from the front to the rear may be provided on the inner wall of attaching part 21a, a convex part (or a groove) matching the groove (or the convex part) may be provided on the surface of the holder of blood sampling cartridge 22, and blood sampling cartridge 22 may be inserted by sliding in this groove (the convex part).

Further, it is also possible to provide a concave part (or a convex part) in holding part 30a of plunger 30 and form a convex part (or a concave part) matching the concave part in grip part 25f of lancet 25.

[The Principle of Measuring the Blood Sugar Level]

Figure 18:
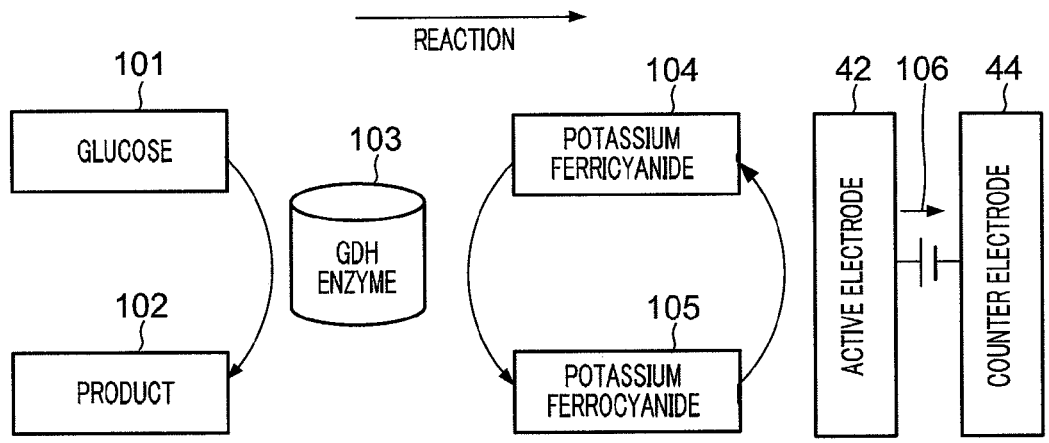
FIG. 18 shows a principle of glucose measurement in blood, of the blood test apparatus.

FIG. 18 shows the measurement principle of blood test apparatus 20 that measures the blood sugar level of blood. Glucose 101 in blood reacts with glucose dehydrogenase (GDH) 103 specifically to give product 102, and potassium ferricyanide 104 is reduced to generate potassium ferrocyanide 105.

The amount of generated potassium ferrocyanide 105 is proportional to the concentration of glucose 101. Potassium herrocyanide 105 is oxidized on detection electrode 42 (see FIG. 15) as an active electrode, and, at this time, oxidation response current 106 flowing toward detection electrode 44 as a counter electrode is proportional to the concentration of glucose 101. Therefore, the blood sugar level can be measured based on this oxidation response current 106.

Figure 19:
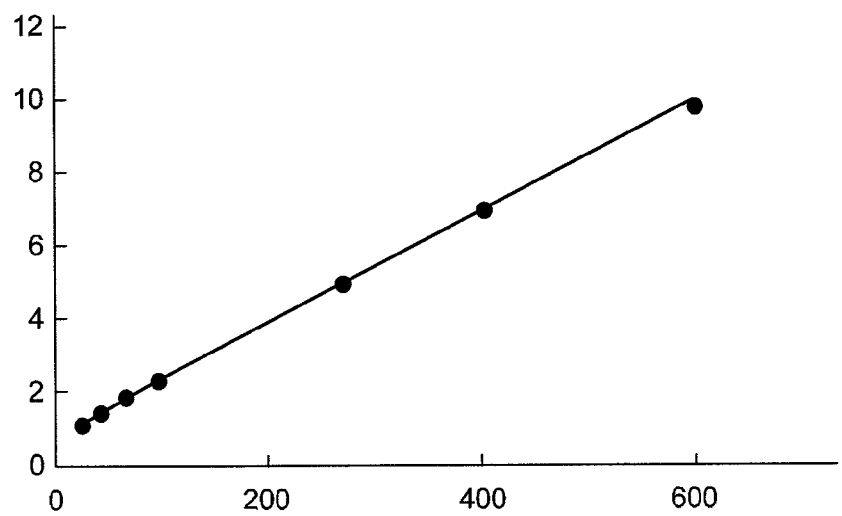
FIG. 19 is a characteristic diagram of glucose measurement.

FIG. 19 shows an output example of the measurement result of blood test apparatus 20. The horizontal axis shows the concentration (mg/dL) of glucose 101, and the vertical axis shows response current 106 (μA). In this way, oxidation response current 106 is proportional to the concentration of glucose 101.

[Test Process]

Figure 20A:
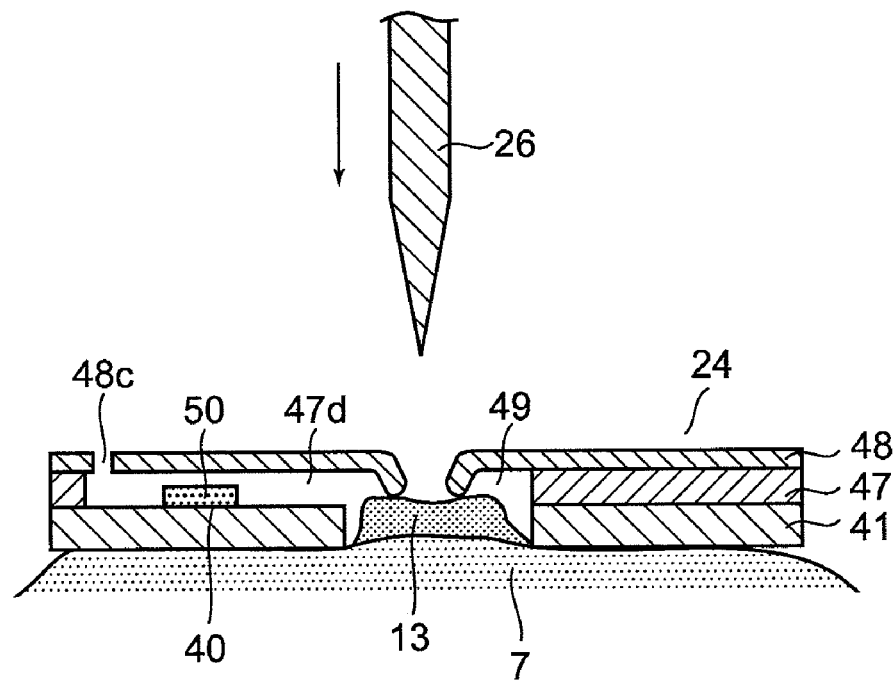
FIG. 20A shows a relationship between the blood sensor and the operation of the blood collection needle.

FIG. 20 shows the relationship between blood collection needle 26 and blood sensor 24 upon blood sampling by the blood test apparatus. As shown in FIG. 20A, substrate 41 of blood sensor 24 abuts on the skin of the patient (such as the skin of a finger). When blood collection needle 26 is shot in the direction of the arrow, blood collection needle 26 projects from blood sensor 24, and breaks through cover 48 in case that there is no opening part in cover 48 forming the upper side of storing part 49, and further, punctures skin 7. Blood 13 flows out from punctured skin 7, and the outflow of blood 13 is led to storing part 49. Blood 13 led to storing part 49 flows into supply channel 47d, and, further, led to detecting section 40 by capillary action.

When the surface of substrate 41, that contacts with the skin, is subjected to water-repellency treatment, the blood flowing out from the skin can be led to storing part 49 efficiently.

Blood 13 is more likely to flow into supply channel 47d, the inner surface of which is subjected to hydrophilicity treatment. When the inner surface of storing part 49 is less hydrophilic than the inner surface of supply channel 47d, blood 13 is more likely to flow into supply channel 47d. Further, when the upper surface of cover 48 is subjected to water-repellency treatment, the outflow of blood 13 from puncturing hole 52a is minimized, so that blood 13 is more likely to flow into supply channel 47d.

Figure 20B:
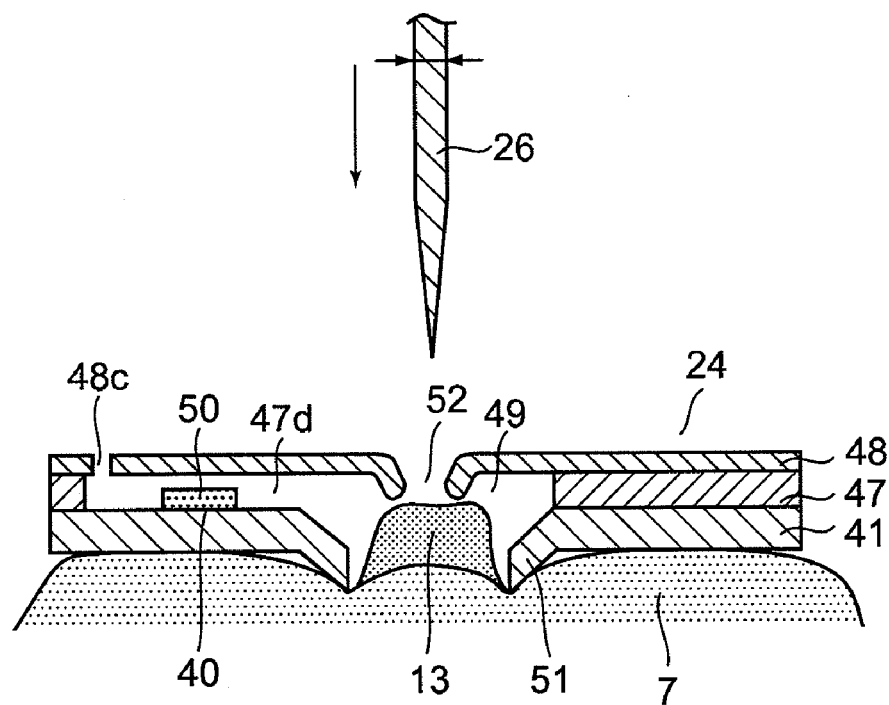
FIG. 20B shows a relationship between the blood sensor to which the bank is provided and the operation of the blood collection needle.

FIG. 20B shows the relationship between blood collection needle 26 and blood sensor 24 in which bank 51 is formed. As shown in FIG. 19, when sensor 24 is made to abut on skin 7 such as a finger of the patient and blood collection needle 26 is shot in the direction of the arrow, skin 7 is punctured and blood 13 flows out in the same way as in FIG. 20A. The outflow of blood 13 fills storing part 49.

At this time, bank 51 is formed near the opening, and so bank 51 is in close contact with skin 7. Therefore, blood 13 flowing out from skin 7 is more likely to be led to storing part and less likely to leak.

FIG. 21 shows cross-sectional views of blood sampling cartridge 22 and attaching part 21a of blood test apparatus 20 into which blood sampling cartridge 22 is inserted. As shown in FIG. 21, inside cylindrically-shaped attaching part 21a, plunger 30 is provided slidably in the front-back direction (in the figure, in the horizontal direction). Holding part 30a of plunger 30 holds grip part 25f of lancet 25 included in blood sampling cartridge 22. Further, blood sampling cartridge 22 is held by elasticity of end 21b of attaching part 21a.

The position where blood sampling cartridge 22 is fixed at attaching part 21a, is specified by a joint between positioning concave part 21h provided in the cylinder of attaching part 21a and positioning convex part 23h provided in holder 23 forming blood sampling cartridge 22. By this means, blood sampling cartridge 22 is fixed at a specified position of attaching part 21a. The contact parts (including the reference contact part) of blood sensor 24 contact with connectors 27, respectively. Terminals 33 are connected to connectors 27, respectively.

Figure 21A:
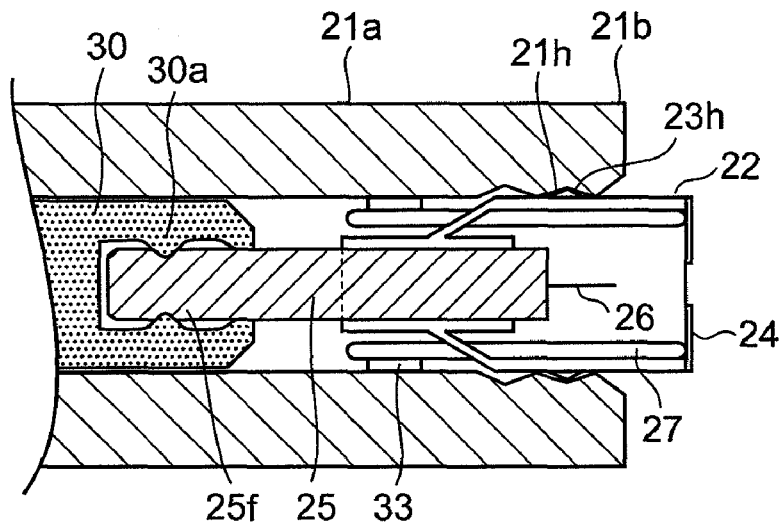
FIG. 21A is a cross-sectional view showing a state of the lancet before puncturing in a state where the blood sampling cartridge is attached to the blood test apparatus.

FIG. 21A shows a state where plunger 30 is pulled backward, and blood collection needle 26 is inside blood sampling cartridge 22. That is, FIG. 21A shows a state before puncturing.

Figure 21B:
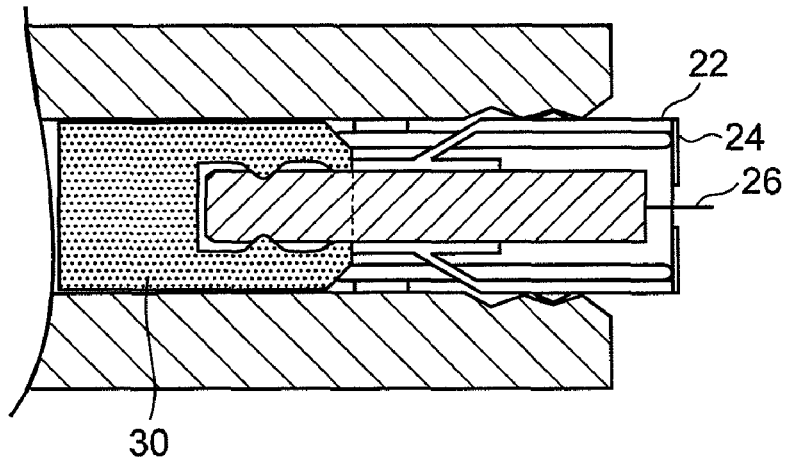
FIG. 21B is a cross-sectional view showing a state of the lancet upon sampling blood.

FIG. 21B shows a state where plunger 30 projects forward. Blood collection needle 26 projects from blood sensor 24 (or blood sensor 24a). In this state, blood is sampled by puncturing the patient's skin.

Figure 21C:
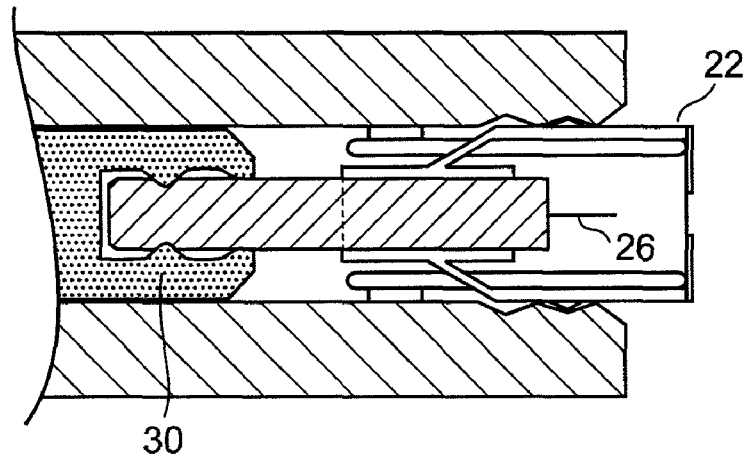
FIG. 21C is a cross-sectional view showing a state of the lancet after sampling blood.

FIG. 21C shows a state where plunger 30 is pulled backward. Blood collection needle 26 is accommodated in blood sampling cartridge 22. Except for the state where plunger 30 projects forward, blood collection needle 26 is accommodated in blood sampling cartridge 22, so that blood collection needle 26 does not puncture the skin by error and is secure, and, further does not make the patient feel fear. Further, blood collection needle 26 does not allow direct touch, and so is secure.

Figure 22:
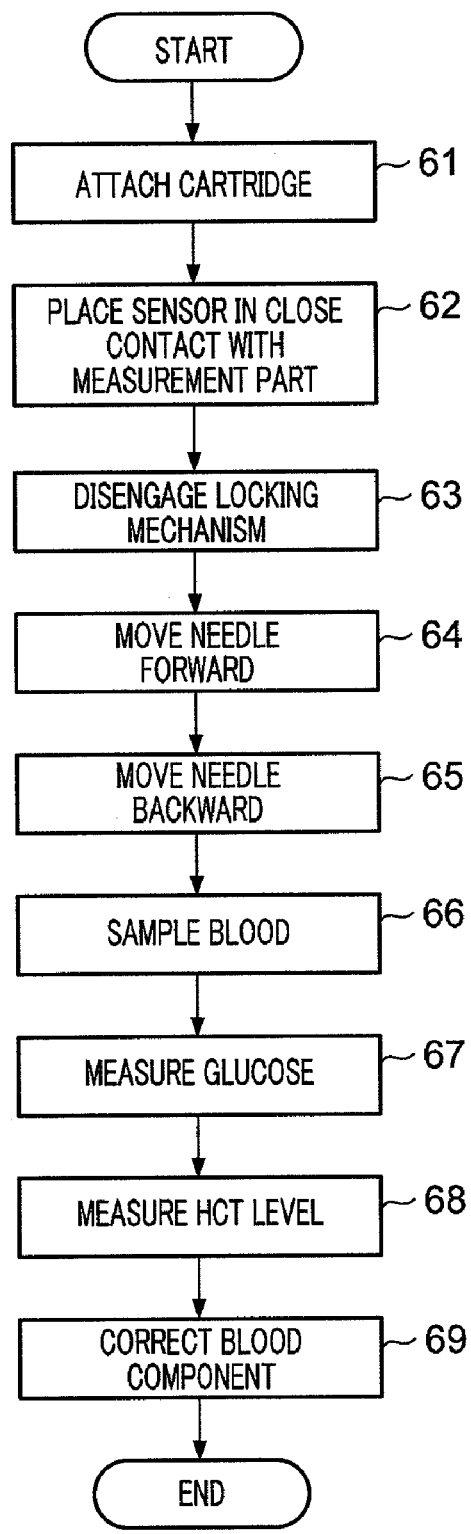
FIG. 22 shows a flow of glucose measurement using the blood test apparatus.

FIG. 22 shows an example of the flow of the test using blood test apparatus 20. In step 61, blood sampling cartridge 22 is inserted into attaching part 21a to be attached to blood test apparatus 20. By this insertion, holder 23 is pressed into attaching part 21a and latched, and positioning concave part 21h and positioning convex part 23h are jointed to determine the position. Further, grip part 25f of lancet 25 is held by holding part 30a of plunger 30.

In step 62, blood sensor 24 of blood sampling cartridge 22 is pressed against the patient's skin and placed in close contact with the patient's skin. In step 63, a locking mechanism of plunger 30, formed by latch convex part 31c provided in handle 31 and latch concave part 21d provided in housing 21, is disengaged. In step 64, blood collection needle 26 attached to lancet 25 projects toward the skin by plunger 30 urged by the spring.

In step 65, after the patient's skin is punctured with blood collection needle 26, blood collection needle 26 is moved backward and accommodated in blood sampling cartridge 22. In step 66, blood flows out and is sampled. The outflow of blood is brought to blood sensor 24 and led to detecting section 40 placed inside supply channel 47d. Then, after detection electrode 43 as a sensing electrode determines that blood of the amount necessary for measurement is led to the detecting section, sampling blood is finished. In this way, blood is not sampled more than necessary, so that it is possible to alleviate the load on the patient significantly.

In step 67, the glucose in the sampled blood is measured. After the glucose in the blood and a glucose oxidation-reduction enzyme are reacted for a certain period, a voltage is applied between detection electrode 42 as an active electrode and detection electrode 44 as a counter electrode. The mediator in a reduction condition, produced on detection electrode 42 by enzyme reaction, is oxidized, and its oxidation current is detected. The reaction time of a glucose and an oxidation-reduction enzyme is normally 10 seconds or less, the voltage applied in step 67 is normally 0.2 to 0.5 V, and the application time is normally 5 seconds or less. This application time is measured by timer 79 (described later).

In step 68, the hematocrit (Hct) level is measured. When a voltage is applied between detection electrode 45 as an active electrode and detection electrode 42 as a counter electrode, a current that depends on the Hct level is detected. The Hct level is measured based on the detected current. The measured Hct level is used to correct the result of measuring the glucose. The relationship between the current and the Hct level may be calculated in advance as a calibration curve, and the detected current may be applied as is.

Generally, the voltage applied in step 68 is approximately 2 to 3 V, and the application time is approximately 5 seconds or less. A mediator is not provided at detection electrode 45, which is an active electrode, there is a certain interval between detection electrode 45 and detection electrode 42, and only blood exists in this interval. Therefore, in step 68, an oxidation current that depends on the Hct level can be detected without being influenced by reagent 50.

Then, in step 69, the measurement result of the blood components is corrected. That is, using the Hct level measured in step 68, the glucose content calculated in step 67 is corrected. This correction is performed based on the calibration curve (including a calibration table) created in advance. The corrected glucose content is displayed on display section 75 of blood test apparatus 20.

After going through steps 67, 68 and 69 of blood sugar level measurement, used blood sampling cartridge 22 is collected or discarded every measurement.

[A Block Diagram of the Blood Test Apparatus]

Figure 23:
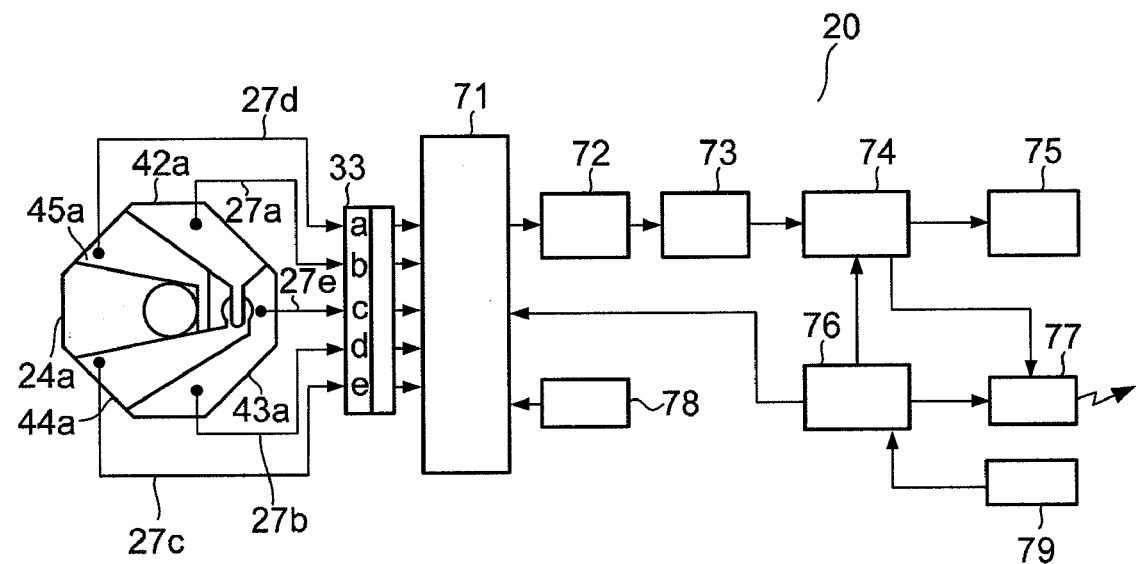
FIG. 23 is a block diagram of the blood test apparatus.

FIG. 23 is a block diagram of blood test apparatus 20. The same components will be assigned the same reference numerals for ease of explanation. Blood test apparatus 20 in FIG. 23 has blood sensor 24a shown in FIG. 16. Connection electrodes 42a to 45a of blood sensor 24a are connected to terminals 33a to 33e. Terminals 33a to 33e are connected to switch circuit 71, and the output of switch circuit 71 is connected to the input of current/voltage converter 72. The output of current/voltage converter 72 is connected to the input of calculating section 74 via analogue/digital converter (hereinafter A/D converter) 73. The output of calculating section 74 is connected to display section 75 (for example, a liquid crystal display device) and also connected to the input of transmitting section 77.

Further, reference voltage supply 78 is connected to switch circuit 71. Reference voltage supply 78 may be a ground potential. The output of controlling section 76 is connected to a control terminal of switch circuit 71, calculating section 74, transmitting section 77 and timer 79.

When a test is conducted using blood test apparatus 20 adopting blood sensor 24a, it is necessary to specify which of terminals 33a to 33e connection electrodes 42a to 45a are connected to, before measuring the blood components. Therefore, by the command of controlling section 76, out of terminals 33a to 33e, terminals having conductivity with the neighboring terminals are specified. When a terminal having conductivity is specified, the electrode connected to the terminal is determined to be connection electrode 43a. Based on the terminal connected to connection electrode 43a as a reference, terminals connected to connection electrodes 44a, 45a and 42a, are determined in that order.

In this way, after the terminals connected to connection electrodes 42a to 45a are determined, the blood components are measured. When blood sensor 24 (see FIG. 15) not having a reference electrode is used, terminals connected to connection electrodes 42a to 45a have already been determined, and so such a step is not necessary.

Next, switch circuit 71 is switched so that detection electrode 42 as an active electrode for measuring the amount of blood components is connected to current/voltage converter 72 via terminal 33. On the other hand, detection electrode 43 which serves as a sensing electrode for detecting the inflow of blood is connected to reference voltage supply 78 via terminal 33. A certain voltage is applied between detection electrode 42 and detection electrode 43. When the blood is led to the detecting section in this state, a current flows between detection electrode 42 and detection electrode 43. This current is converted to a voltage by current/voltage converter 72, and the voltage value is converted to a digital value by A/D converter 73. The digital value is outputted to calculating section 74. Calculating section 74 detects the inflow of blood based on the digital value.

Next, the amount of blood components (glucose) is measured. The glucose content is measured by, first, switching switch circuit 71 by the command of controlling section 76 so that detection electrode 42, which is an active electrode for measuring the glucose content, is connected to current/voltage converter 72 via terminal 33. On the other hand, detection electrode 44, which is a counter electrode for measuring the glucose content, is connected to reference voltage supply 78 via terminal 33.

While the glucose in blood and the oxidation-reduction enzyme are reacted for a certain period, current/voltage converter 72 and reference voltage supply 78 may be turned off. After the glucose in blood and the oxidation-reduction enzyme are reacted for a certain period (10 seconds or less), when a certain voltage (0.2 to 0.5 V) is applied between detection electrodes 42 and 44 by the command of controlling section 76, a current flows between detection electrode 42 and detection electrode 44. This current is converted to a voltage by current/voltage converter 72, and the voltage value is converted to a digital value by A/D converter 73 and outputted to calculating section 74. Calculating section 74 converts the digital value to a glucose content.

After the glucose content is measured, the Hct level is measured. First, by the command of controlling section 76, switch circuit 71 is switched to connect detection electrode 45, which is an active electrode for measuring the Hct level, to current/voltage converter 72 via terminal 33. On the other hand, detection electrode 42, which is a counter electrode for measuring the Hct level, is connected to reference voltage supply 78.

Then, by the command of controlling section 76, a certain voltage (2 to 3 V) is applied between detection electrode 45 and detection electrode 42 from current/voltage converter 72 and reference voltage supply 78. The current flowing between detection electrode 45 and detection electrode 42 is converted to a voltage by current/voltage converter 72, and the voltage value is converted to a digital value by A/D converter 73 and outputted to calculating section 74. Calculating section 74 measures the Hct level based on the digital value.

From the measured Hct level and the glucose content, the glucose content is corrected with the Hct level with reference to the calibration curve or the calibration table. The result after correction may be displayed on display section 75 or transmitted to an injection apparatus that injects a curative drug (for example, insulin) from transmitting section 77. The result after correction may be transmitted by radio, but is preferably transmitted using optical communication which does not interfere with medical equipment.

In case that the injection apparatus for injecting curative drug can set a dose of the curative drug automatically based on the result after correction (measured data) transmitted from transmitting section 77, the patient does not have to set a dose of the curative drug, which eliminates the inconvenience of setting a dose. Further, the amount of insulin can be set for the injection apparatus without involving an artificial means, so that it is possible to prevent setting errors.

[The Negative Pressure Means]

The blood test apparatus of the present invention may have a negative pressure means. By the negative pressure means, a negative pressure is preferably applied near the part of the skin punctured with blood collection needle 26. Therefore, blood test apparatus 20 with the negative pressure means preferably has a member for surrounding the neighborhood of the punctured part of the skin, and may apply a negative pressure to the space surrounded by the member.

Figure 24:
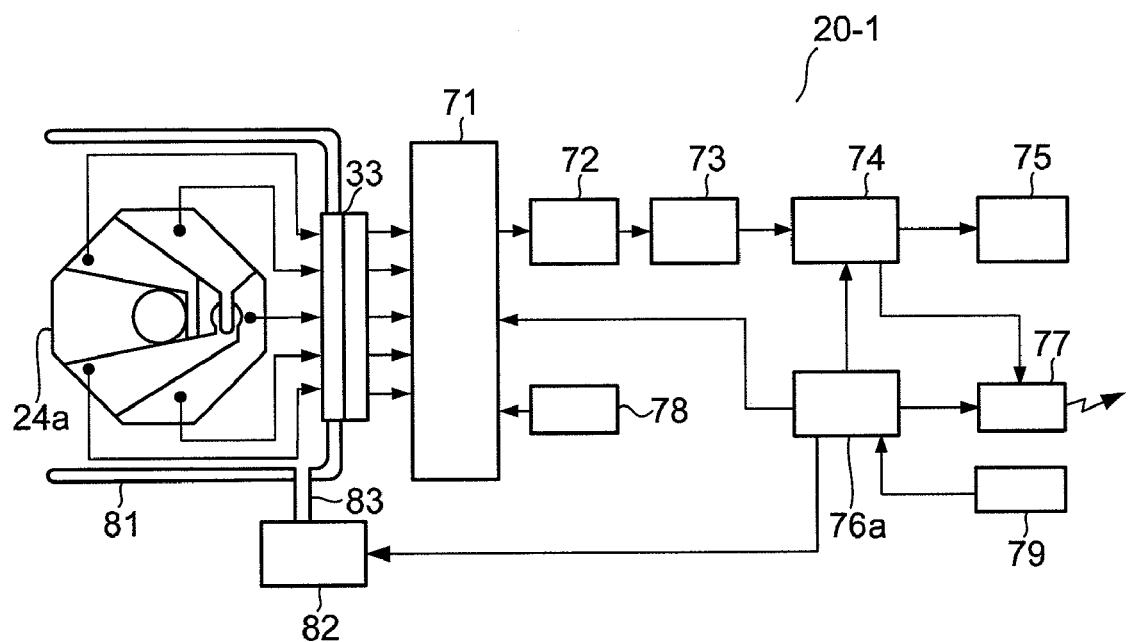
FIG. 24 is a block diagram of the blood test apparatus having a negative pressure means.

FIG. 24 is a block diagram of blood test apparatus 20-1 with a negative pressure means. Blood test apparatus 20-1 is different from blood test apparatus 20 shown in FIG. 23 in that blood test apparatus 20-1 has a negative pressure means, and so the difference will be mainly described. The same components as blood test apparatus 20 will be assigned the same reference numerals for ease of explanation.

In FIG. 24, guard member 81 is provided so as to extend from end 21b of attaching part 21a. Controlling section 76a is connected to negative pressure section 82 (for example, a vacuum generator), and the output of negative pressure means 82 is connected inside of guard member 81 via negative pressure path 83. Therefore, negative pressure can be applied inside of guard member 81 by negative pressure means 82.

Negative pressure means 82 may be started up after step 62 in which blood sensor 24a (which may be blood sensor 24) is made close contact with the measurement part, and stopped after step 66 in which blood is sampled. Upon sampling blood, by applying a negative pressure to the space between the skin punctured with the blood collection needle and blood sensor 24a, the skin is put under a state of tension so as to enable fast and reliable blood sampling.

Figure 25A:
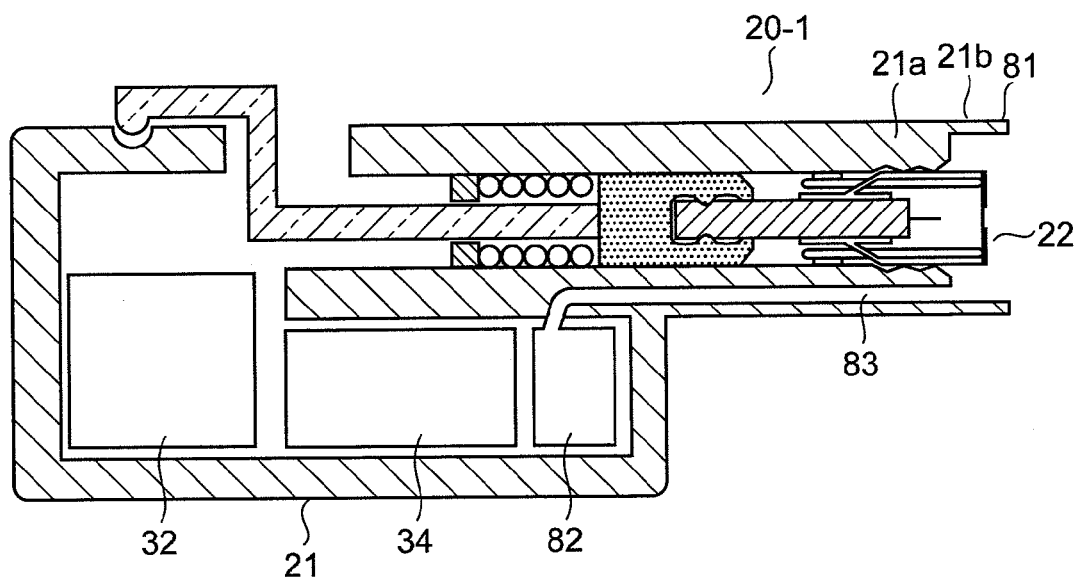
FIG. 25A is a cross-sectional view of the blood test apparatus having the negative pressure means.

FIG. 25A shows a cross-sectional view of blood test apparatus 20-1. In FIG. 25A, guard member 81 is provided so as to extend from end 21b of attaching part 21a. The output of negative pressure means 82 (for example, a vacuum generator) connected to controlling section 76a is connected inside guard member 81 via negative pressure path 83. Therefore, negative pressure means 82 can apply a negative pressure inside guard member 81.

Figure 25B:
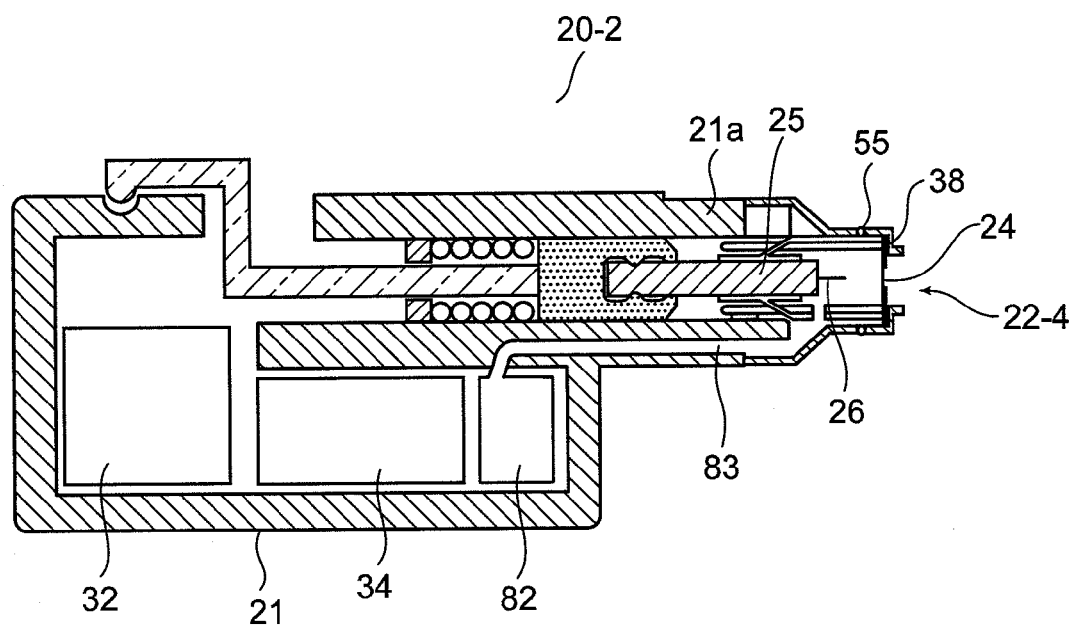
FIG. 25B is a cross-sectional view of another blood test apparatus having the negative pressure means.
Figure 26:
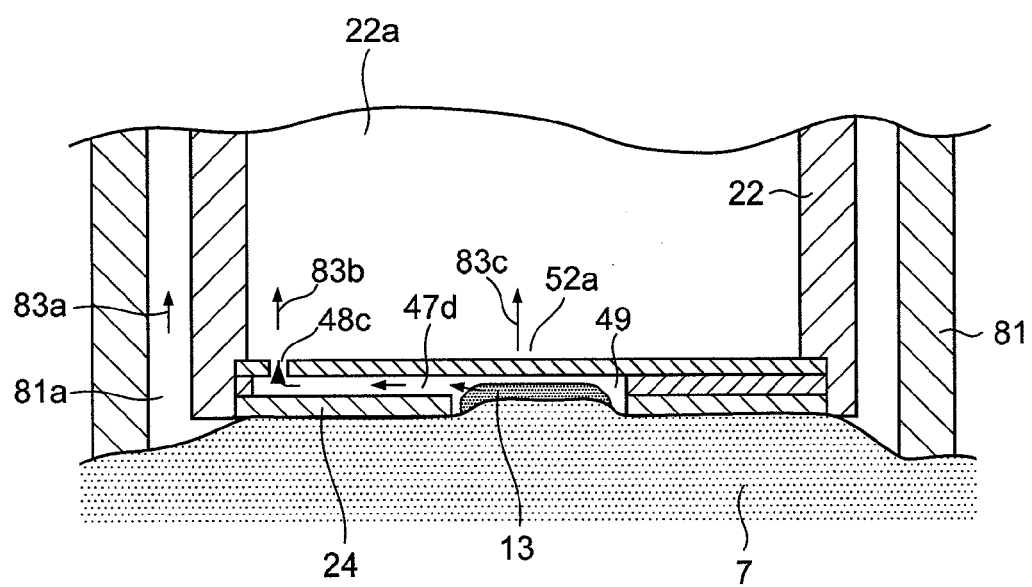
FIG. 26 is a cross-sectional view near the blood sensor of the blood test apparatus having the negative pressure means.

FIG. 26 is a cross-sectional view that expands the main part near guard member 81 of blood test apparatus 20-1. In FIG. 25, as a result of the operation of negative pressure means 82, air pressure within inner part 81a of guard member 81 is reduced as shown by arrow 83a, and skin 7 is brought in close contact with sensor 24 of guard member 81 and put under a state of tension. At this time, air pressure within inner part 22a of blood sampling cartridge 22 is also reduced.

Before puncturing with blood collection needle 26 (see FIG. 20), skin 7 is preferably plumped up by inspiring air in the inner part of storing part 49 in a direction of arrow 83b through air hole 48c so as to apply negative pressure to the inner part. By this means, skin 7 is put under a state of tension to make puncturing easier.

After puncturing with blood collection needle 26, air in the inner part of storing part 49 is inspired through puncturing hole 36 in addition to air hole 48c as shown by arrow 83c, and a negative pressure is further applied to further plumped skin 7 and help blood 13 to be sampled.

In this way, air hole 48c and blood supply channel 47d are also used as supply channels for negative pressure, so that it is possible to apply a negative pressure to the inner part of storing part 49 without providing a separate supply channel for negative pressure. Further, after puncturing, puncturing hole 52a can be also used as a supply channel for negative pressure.

Guard member 81 in blood test apparatus 20-1 with the negative pressure means shown in FIG. 24, FIG. 25A and FIG. 26 may be used as second holder 38 shown in above-described FIG. 2B. When second holder 38 is used, the negative pressure means may apply a negative pressure to space formed by circular projecting part 38a of second holder 38 and the skin.

FIG. 25B is a cross-sectional view showing a state where blood sampling cartridge 22-4 (the same also applies to a case of blood sampling cartridge 22-2) with second holder 38 is attached to housing 21 of blood test apparatus 20-2. How blood sampling cartridge 22-4 is attached to attaching part 21a of housing 21 is shown in FIG. 8A to FIG. 8E. In FIG. 25B, negative pressure path 83 is formed in housing 21 and connected to the inside of blood sampling cartridge 22-4. By this means, it is possible to plump up the skin upon puncturing and sample blood fast after puncturing.

FIG. 27 shows a state where the patient tries to examine blood using blood test apparatus 20. The patient is trying to sample the blood from the index finger of the patient's left hand and measure blood components (for example, the blood sugar level). In blood test apparatus 20, attaching part 21a is provided in one side of housing 21. Blood sampling cartridge 22 is inserted and fixed at attaching part 21a, and blood sensor 24 is attached to one end of blood sampling cartridge 22. Further, display section 75 is provided in the other side of housing 21. As a mechanism for driving plunger 30, for example, the method disclosed in Japanese Patent Application Laid-Open No. 2006-314718 can be adopted. By this means, it is possible to realize a mechanism for preventing sticking twice and a mechanism for adjusting the depth of puncturing.

Further, blood test apparatus 20 may have a mechanism for adjusting the depth of puncturing, and, as an example of this mechanism, FIG. 27 shows puncturing depth adjusting control 84.

The blood test apparatus of the present invention can be used to measure a glucose, and also is suitable for measuring blood components such as the lactate level and cholesterol.

INDUSTRIAL APPLICABILITY

The blood test apparatus of the present invention can attach and remove a blood sampling cartridge including a blood collection needle and a blood sensor in a simple manner, and is applicable to medical equipment, and the like.

The disclosures of Japanese Patent Application No. 2006-000354, Japanese Patent Application No. 2006-000355, Japanese Patent Application No. 2006-000356, Japanese Patent Application No. 2006-000357 and Japanese Patent Application No. 2006-000358, filed on Jan. 5, 2006, and Japanese Patent Application No. 2006-022040, filed on Jan. 31, 2006, including the specifications, drawings and abstracts are incorporated herein by reference in its entirety.

The invention claimed is:

1. A blood test apparatus comprising:
a housing;
a measuring circuit accommodated in the housing;
two or more connectors electrically connected to the measuring circuit;
an attaching part formed in one side of the housing;
a plunger that moves back and forth in the housing;
a lancet, one end of the lancet is held by the plunger so as to allow the one end to be inserted into and removed from the plunger;
a blood collection needle attached to the other end of the lancet;

a holder that is held by the attaching part so as to allow the holder to be inserted into and removed from the attaching part and that allows the lancet to move inside the holder; and a blood sensor that is attached to one end of the holder and that has two or more connection electrodes, wherein:

the lancet, the blood collection needle and the blood sensor are integrated with the holder to constitute a blood sampling cartridge that can be detachably inserted into and removed from the attaching part;

two or more connectors are arranged so as to be in contact with the connection electrodes of the blood sensor, contact parts of the two or more connectors that contact with the connection electrodes of the blood sensor are arranged around a specific point and arranged at equi-angular intervals centered on the specific point;

the specific point is a center of rotation with respect to an axis of an insertion direction for attaching the blood sampling cartridge to the attaching part;

one of the two or more connection electrodes includes a reference electrode; and wherein the measuring circuit determines the positions of the two or more connectors relative to the two or more connection electrodes by determining which of the two or more connection electrodes includes the reference electrode and identifying which of the two or more connection electrodes contacts which of the two or more connectors.

2. The blood test apparatus according to claim 1, wherein an outer surface of the holder and an inner surface of the attaching part comprise a guide for inserting and removing the blood sampling cartridge.

3. The blood test apparatus according to claim 1, wherein a front part of the holder of the blood sampling cartridge with respect to an insertion direction is thinner than a rear part.

4. The blood test apparatus according to claim 1, wherein the blood collection needle and the lancet of the blood sampling cartridge are integrated.

5. The blood test apparatus according to claim 1, wherein the blood sampling cartridge is divisible into the integrated blood collection needle and lancet, and the holder to which the blood sensor is attached.

6. The blood test apparatus according to claim 1, wherein the blood sensor comprises:

a base plate;

a storage that is provided in the base plate and that samples blood from a skin punctured with the blood collection needle;

a supply channel, one end of which is connected to the storage, and, into which blood in the storage flows by capillary action;

a detector provided in the supply channel; and an air hole that communicates with the supply channel.

7. The blood test apparatus according to claim 6, wherein:

the storage provided in the base plate comprises an opening in a surface that abuts the skin and a closing part in a surface opposite the surface that abuts the skin; and the closing part is puncturable with the blood collection needle.

8. The blood test apparatus according to claim 7, wherein an area of the air hole is smaller than an area punctured with the blood collection needle.

9. The blood test apparatus according to claim 7, wherein a diameter of the air hole is 10 to 80 percent of a diameter of the blood collection needle.

10. The blood test apparatus according to claim 6, wherein the storage provided in the base plate comprises:

a first opening in a surface that abuts the skin; and a second opening through which the blood collection needle can pass, in an surface opposite the surface that abuts the skin.

11. The blood test apparatus according to claim 10, wherein an area of the air hole is smaller than an area of the second opening.

12. The blood test apparatus according to claim 10, wherein an area of the second opening is larger than an area of the air hole and smaller than an area of the first opening.

13. The blood test apparatus according to claim 10, wherein the blood sampling cartridge comprises a cap that covers the blood collection needle of the lancet, and the cap passes through the storage.

14. The blood test apparatus according to claim 6, wherein at least part of the base plate is formed with a transparent member, so that blood inside the supply channel is visible.

15. The blood test apparatus according to claim 6, further comprising a second holder that covers a surface of the base plate, which surface abuts on the skin, wherein the second holder comprises a round concave part of 4 to 15 mm in diameter on the surface that abuts the skin.

16. The blood test apparatus according to claim 6, wherein:

the detector comprises two or more detection electrodes configured to detect components of the sampled blood and a reagent, the two or more detection electrodes are connected to the two or more connection electrodes, respectively.

17. The blood test apparatus according to claim 16, wherein the reference electrode is electrically connected to one of the two or more connection electrodes via a conductor.

18. The blood test apparatus according to claim 16, wherein the reference electrode is electrically insulated from one of the two or more connection electrodes.

19. The blood test apparatus according to claim 16, wherein the reference electrode is identified by measuring resistance values between the reference electrode and each of the two or more connection electrodes.

20. The blood test apparatus according to claim 6, wherein a negative pressure can be supplied to the storage via the air hole.

21. The blood test apparatus according to claim 6, wherein a volume of the storage is one to twenty times a volume of the supply channel.

22. The blood test apparatus according to claim 6, wherein a volume of the storage is four to fifteen times a volume of the supply channel.

23. The blood test apparatus according to claim 6, wherein:

the base plate comprises:

a substrate that defines part of the storage;

a spacer that is provided on the substrate and that defines the supply channel and part of the storage; and a cover that is provided on an upper surface of the spacer and in which the air hole is provided; and a thickness of the substrate is greater than a thickness of the spacer.

24. The blood test apparatus according to claim 6, wherein a hydrophilicity treatment is applied to an inner surface of the supply channel, and a water repellent treatment is applied to a back surface of the base plate, wherein a front surface of the base plate abuts the skin.

25. The blood test apparatus according to claim 24, wherein an upper surface of the storage is less hydrophilic than an inner surface of the supply channel.

26. The blood test apparatus according to claim 24, wherein an upper surface of the storage is less water repellent than the back surface of the base plate.

27. The blood test apparatus according to claim 6, wherein a water repellent treatment is applied near the storage in a front surface of the base plate, which front surface abuts the skin.

28. The blood test apparatus according to claim 27, wherein a water repellent treatment is applied to an entire front surface of the base plate.

29. The blood test apparatus according to claim 27, wherein a water repellent treatment is applied to a back surface of the base plate, wherein the front surface abuts the skin.

30. The blood test apparatus according to claim 6, wherein an upper surface of the storage is less water repellent than a part near the storage on a front surface of the base plate, which front surface abuts the skin.

31. The blood test apparatus according to claim 6, wherein a projecting bank is provided near an opening of the storage on a front surface of the base plate, which front surface abuts the skin.

32. The blood test apparatus according to claim 31, wherein the bank is integrated with the base plate.

33. The blood test apparatus according to claim 31, wherein the bank is a separate member from the base plate.

34. The blood test apparatus according to claim 31, wherein:
   the base plate comprises:
      a substrate that defines part of the storage;
      a spacer that is provided on the substrate and that defines the supply channel and part of the storage; and
      a cover which is provided on an upper surface of the spacer, and in which the air hole is provided; and
   the base plate is manufactured by:
      preparing the substrate where the bank is formed near the opening of the storage;
      stacking the spacer on a surface of the substrate where the bank is not formed; and
      stacking the cover on the spacer.

35. The blood test apparatus according to claim 1, further comprising a negative pressure supplier that applies a negative pressure near part of the skin punctured with the blood collection needle.

36. The blood test apparatus according to claim 1, further comprising a display that displays a measurement result at the measuring circuit, or a transmitter that transmits the measurement result.

37. A blood sampling cartridge that is removably attachable to the blood test apparatus according to claim 1.

* * * * *